United States Patent
Yoshida et al.

(10) Patent No.: US 11,359,180 B2
(45) Date of Patent: Jun. 14, 2022

(54) METHOD FOR PRODUCING MYOCARDIAL CELLS USING SYNTHETIC PEPTIDE

(71) Applicants: Toagosei Co., Ltd., Tokyo (JP); KYOTO UNIVERSITY, Kyoto (JP)

(72) Inventors: Tetsuhiko Yoshida, Ibaraki (JP); Kenichi Tanaka, Ibaraki (JP); Nahoko Baileykobayashi, Ibaraki (JP); Yoshinori Yoshida, Kyoto (JP)

(73) Assignees: Toagosei Co., Ltd., Tokyo (JP); Kyoto University, Kyoto (JP)

(*) Notice: Subject to any disclaimer, the term of this patent is extended or adjusted under 35 U.S.C. 154(b) by 175 days.

(21) Appl. No.: 15/569,887

(22) PCT Filed: Apr. 28, 2016

(86) PCT No.: PCT/JP2016/063411
§ 371 (c)(1),
(2) Date: Oct. 27, 2017

(87) PCT Pub. No.: WO2016/175303
PCT Pub. Date: Nov. 3, 2016

(65) Prior Publication Data
US 2018/0127727 A1    May 10, 2018

(30) Foreign Application Priority Data

Apr. 28, 2015  (JP) .............. JP2015-092087

(51) Int. Cl.
| | | |
|---|---|---|
| C12N 5/16 | (2006.01) |
| C07K 14/00 | (2006.01) |
| C07K 14/47 | (2006.01) |
| C07K 14/475 | (2006.01) |
| C07K 14/575 | (2006.01) |
| C12N 5/0735 | (2010.01) |
| C12N 5/077 | (2010.01) |
| C12N 5/074 | (2010.01) |

(52) U.S. Cl.
CPC .............. *C12N 5/16* (2013.01); *C07K 14/00* (2013.01); *C07K 14/475* (2013.01); *C07K 14/4711* (2013.01); *C07K 14/575* (2013.01); *C12N 5/0606* (2013.01); *C12N 5/0657* (2013.01); *C12N 5/0696* (2013.01); *C12N 2506/03* (2013.01); *C12N 2506/14* (2013.01); *C12N 2510/00* (2013.01)

(58) Field of Classification Search
None
See application file for complete search history.

(56) References Cited

U.S. PATENT DOCUMENTS

| | | |
|---|---|---|
| 2009/0068742 A1 | 3/2009 | Yamanaka |
| 2009/0325288 A1 | 12/2009 | Koshimizu et al. |
| 2010/0297758 A1 | 11/2010 | Yoshida et al. |
| 2012/0035112 A1 | 2/2012 | Yoshida et al. |
| 2013/0079273 A1 | 3/2013 | Yoshida et al. |
| 2015/0126434 A1 | 5/2015 | Kobayashi et al. |
| 2016/0326488 A1 | 11/2016 | Tanaka et al. |

FOREIGN PATENT DOCUMENTS

| | | |
|---|---|---|
| EP | 2 263 705 | 12/2010 |
| JP | 2009-165481 | 7/2009 |
| JP | 2009-215191 | 9/2009 |
| JP | 2011-98900 | 5/2011 |
| WO | WO2007/126077 | 11/2007 |
| WO | WO2009/093692 | 7/2009 |
| WO | WO2010/117079 | 10/2010 |
| WO | WO2011/152524 | 12/2011 |
| WO | WO2013/180011 | 12/2013 |
| WO | WO2015/098962 | 7/2015 |

OTHER PUBLICATIONS

Batalov (Biomarker Insights, 10(S1): 1-6, 2015 (Year: 2015).*
Song et al., "Efficient generation of hepatocyte-like cells from human induced pluripotent stem cells" Cell Research vol. 19(11): pp. 1233-1242, 2009.
Shiraki et al., "Ffficent Differentiation of Embryonic Stem Cells into Hepatic Ceils in Vitro Using a Feeder-Free Basement Membrane Substratum" Plos One, vol. 6(8): pp. 1-10, Aug. 2011.
Cai et al., Protocol for directed differentiation of human pluripotent stem cells toward a hepatocyte fate, Stembook, pp. 1-11, 2012.
Cai et al., "Directed Differentiation of Human Embryonic Stem Cells into Functional Hepatic Cells", Hepatology, 45(5): pp. 1229-1239, 2007.
Hay et al., "Efficient Differentiatio of Hepatocytes from Human Embryonic Stem Cells Exhibiting Markers Recapitulating Liver Development In Vivo" Stem Cells, 26: 894-902, 2008.
Tayeb et al., "Highly Efficient Gene ration of Human Hepatocyte-Like Cells from Induced Pluripotent Stem Cells" Hepatology, 51(1): pp. 297-305, 2010.
Dongxin Zhao et al. "Promotion of the efficient metabolic maturation of human pluripotent stem cell-derived hepatocvtes by correcting specification defects", Cell Research, 23(1): pp. 157-161, 2013.

(Continued)

*Primary Examiner* — Anoop K Singh
*Assistant Examiner* — Magdalene K Sgagias
(74) *Attorney, Agent, or Firm* — Occhiuti & Rohlicek LLP

(57) ABSTRACT

Provided is a method for producing myocardial cells from pluripotent stem cells. The myocardial cell production method provided by the present invention includes supplying an artificially produced synthetic peptide to a cell culture that contains pluripotent stem cells. The synthetic peptide is a peptide that contains a myocardial cell differentiation-inducing peptide sequence that induces pluripotent stem cells into myocardial cells. The myocardial cell differentiation-inducing peptide sequence is an amino acid sequence selected from the group consisting of (i) an amino acid sequence constituting the signal peptide of any protein belonging to the amyloid precursor protein (APP) family, (ii) a partial amino acid sequence of the amino acid sequence according to (i), and (iii) a modified amino acid sequence from the amino acid sequence according to (i) or (ii).

14 Claims, 3 Drawing Sheets

Specification includes a Sequence Listing.

(56) References Cited

OTHER PUBLICATIONS

Chen et al., "Rapid Generation of Mature Hepatocyte-Like Cells from Human Induced Pluripotent Stem Cells by an Efficient Three-Step Protocol", Hepatology, 55(4): pp. 1193-1203, 2012.
Shinzou, "Hearts Selection One" 46(12): pp. 1546-1549, 2014.

\* cited by examiner

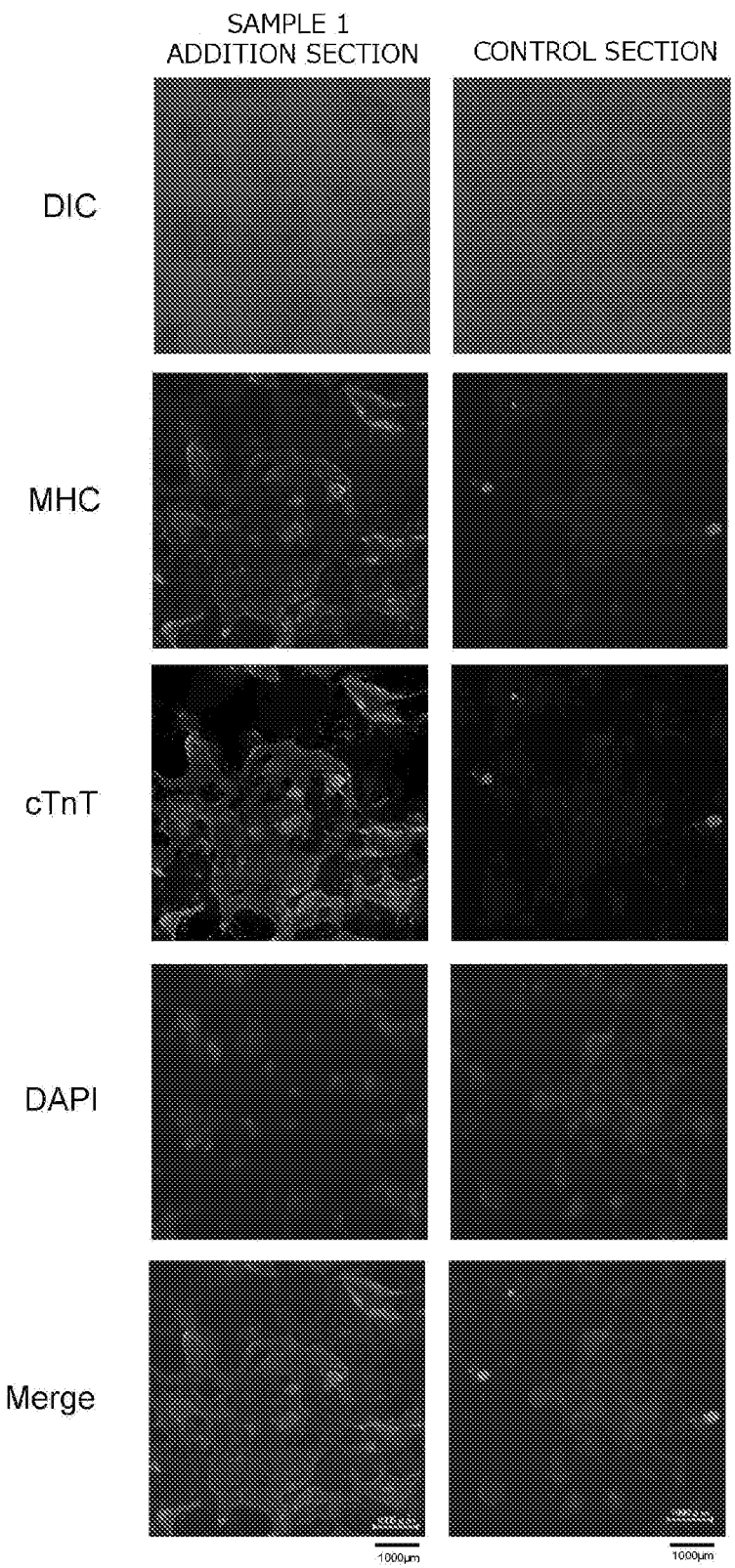

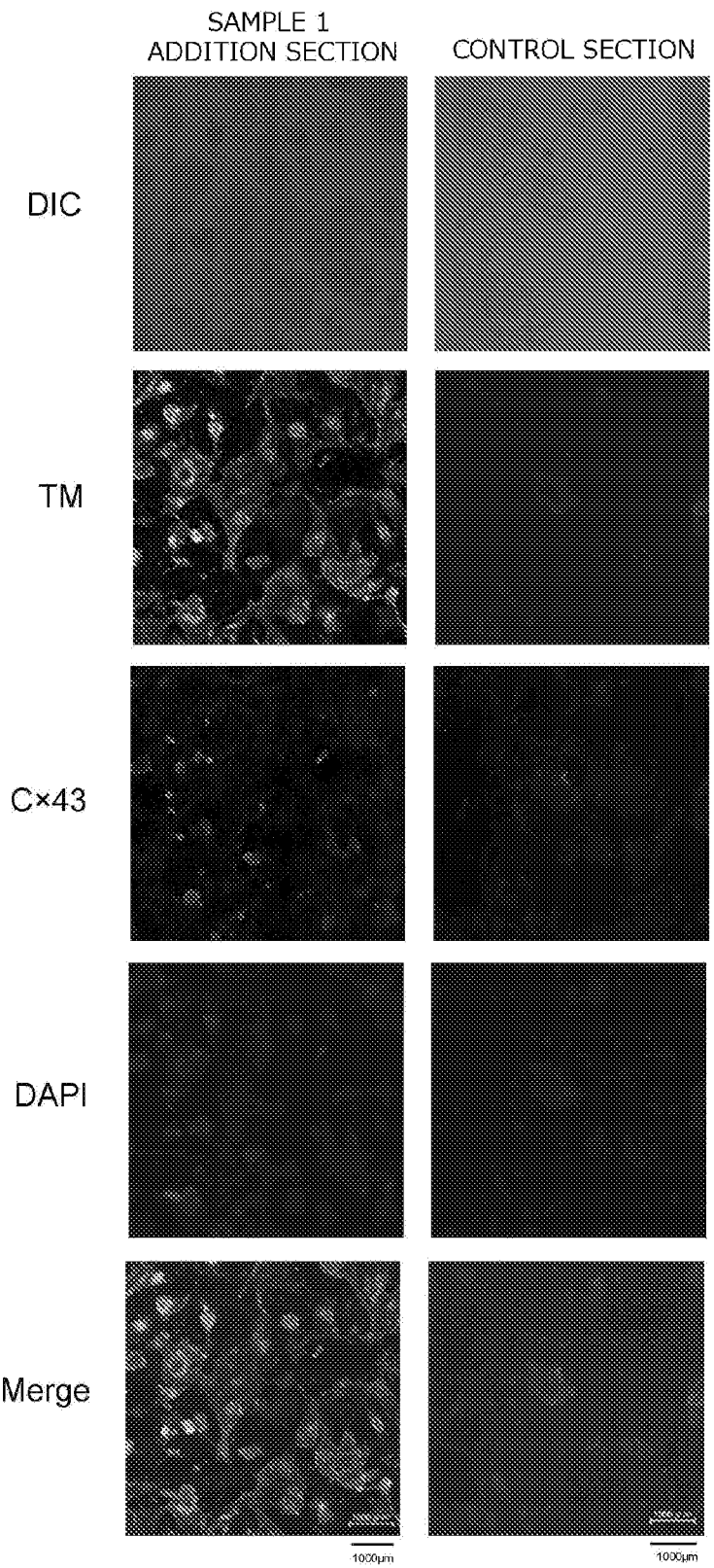

SEQUENCE LISTING

```
<160> NUMBER OF SEQ ID NOS: 26

<210> SEQ ID NO 1
<211> LENGTH: 29
<212> TYPE: PRT
<213> ORGANISM: Artificial sequence
<220> FEATURE:
<223> OTHER INFORMATION: Synthetic peptide

<400> SEQUENCE: 1

Met Ala Ala Thr Gly Thr Ala Ala Ala Ala Ala Thr Gly Arg Leu Leu
1               5                   10                  15
```

Leu Leu Leu Leu Val Gly Leu Thr Ala Pro Ala Leu Ala
            20                  25

<210> SEQ ID NO 2
<211> LENGTH: 29
<212> TYPE: PRT
<213> ORGANISM: Artificial sequence
<220> FEATURE:
<223> OTHER INFORMATION: Synthetic peptide

<400> SEQUENCE: 2

Met Ala Ala Thr Gly Thr Ala Ala Ala Ala Thr Gly Lys Leu Leu
1               5                   10                  15

Val Leu Leu Leu Leu Gly Leu Thr Ala Pro Ala Ala Ala
            20                  25

<210> SEQ ID NO 3
<211> LENGTH: 38
<212> TYPE: PRT
<213> ORGANISM: Artificial sequence
<220> FEATURE:
<223> OTHER INFORMATION: Synthetic peptide

<400> SEQUENCE: 3

Met Gly Pro Ala Ser Pro Ala Ala Arg Gly Leu Ser Arg Arg Pro Gly
1               5                   10                  15

Gln Pro Pro Leu Pro Leu Leu Leu Pro Leu Leu Leu Leu Leu Arg
            20                  25                  30

Ala Gln Pro Ala Ile Gly
        35

<210> SEQ ID NO 4
<211> LENGTH: 37
<212> TYPE: PRT
<213> ORGANISM: Artificial sequence
<220> FEATURE:
<223> OTHER INFORMATION: Synthetic peptide

<400> SEQUENCE: 4

Met Gly Pro Thr Ser Pro Ala Ala Arg Gly Gln Gly Arg Arg Trp Arg
1               5                   10                  15

Pro Pro Leu Pro Leu Leu Leu Pro Leu Ser Leu Leu Leu Leu Arg Ala
            20                  25                  30

Gln Leu Ala Val Gly
        35

<210> SEQ ID NO 5
<211> LENGTH: 17
<212> TYPE: PRT
<213> ORGANISM: Artificial sequence
<220> FEATURE:
<223> OTHER INFORMATION: Synthetic peptide

<400> SEQUENCE: 5

Met Leu Pro Gly Leu Ala Leu Leu Leu Leu Ala Ala Trp Thr Ala Arg
1               5                   10                  15

Ala

<210> SEQ ID NO 6
<211> LENGTH: 17
<212> TYPE: PRT
<213> ORGANISM: Artificial sequence
<220> FEATURE:

-continued

```
<223> OTHER INFORMATION: Synthetic peptide

<400> SEQUENCE: 6

Met Leu Pro Ser Leu Ala Leu Leu Leu Ala Ala Trp Thr Val Arg
1               5                   10                  15

Ala

<210> SEQ ID NO 7
<211> LENGTH: 13
<212> TYPE: PRT
<213> ORGANISM: Artificial sequence
<220> FEATURE:
<223> OTHER INFORMATION: synthetic peptide

<400> SEQUENCE: 7

Lys Lys Arg Thr Leu Arg Lys Asn Asp Arg Lys Lys Arg
1               5                   10

<210> SEQ ID NO 8
<211> LENGTH: 14
<212> TYPE: PRT
<213> ORGANISM: Artificial sequence
<220> FEATURE:
<223> OTHER INFORMATION: Synthetic peptide

<400> SEQUENCE: 8

Arg Ser Arg Lys Tyr Thr Ser Trp Tyr Val Ala Leu Lys Arg
1               5                   10

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Trp Arg Arg Gln Ala Arg Phe Lys
1               5

<210> SEQ ID NO 10
<211> LENGTH: 13
<212> TYPE: PRT
<213> ORGANISM: Artificial sequence
<220> FEATURE:
<223> OTHER INFORMATION: Synthetic peptide

<400> SEQUENCE: 10

Arg Leu Pro Val Arg Arg Arg Arg Arg Val Pro Lys
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic peptide

<400> SEQUENCE: 11

Tyr Gly Arg Lys Lys Arg Arg Gln Arg Arg
1               5                   10

<210> SEQ ID NO 12
<211> LENGTH: 11
<212> TYPE: PRT
<213> ORGANISM: Artificial sequence
```

```
<220> FEATURE:
<223> OTHER INFORMATION: Synthetic peptide

<400> SEQUENCE: 12

Tyr Ala Arg Ala Ala Ala Arg Gln Ala Arg Ala
1               5                   10

<210> SEQ ID NO 13
<211> LENGTH: 16
<212> TYPE: PRT
<213> ORGANISM: Artificial sequence
<220> FEATURE:
<223> OTHER INFORMATION: Synthetic peptide

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Arg Arg Arg Arg Arg Arg Arg Arg Arg
1               5

<210> SEQ ID NO 15
<211> LENGTH: 19
<212> TYPE: PRT
<213> ORGANISM: Artificial sequence
<220> FEATURE:
<223> OTHER INFORMATION: Synthetic peptide

<400> SEQUENCE: 15

Gly Arg Cys Arg Arg Leu Ala Asn Phe Pro Gly Arg Lys Arg Arg
1               5                   10                  15

Arg Arg Arg

<210> SEQ ID NO 16
<211> LENGTH: 13
<212> TYPE: PRT
<213> ORGANISM: Artificial sequence
<220> FEATURE:
<223> OTHER INFORMATION: Synthetic peptide

<400> SEQUENCE: 16

Leu Leu Leu Leu Leu Leu Val Gly Leu Thr Ala Pro Ala
1               5                   10

<210> SEQ ID NO 17
<211> LENGTH: 12
<212> TYPE: PRT
<213> ORGANISM: Artificial sequence
<220> FEATURE:
<223> OTHER INFORMATION: Synthetic peptide

<400> SEQUENCE: 17

Leu Val Leu Leu Leu Leu Gly Leu Thr Ala Pro Ala
1               5                   10

<210> SEQ ID NO 18
<211> LENGTH: 13
<212> TYPE: PRT
```

<213> ORGANISM: Artificial sequence
<220> FEATURE:
<223> OTHER INFORMATION: Synthetic peptide

<400> SEQUENCE: 18

Pro Leu Pro Leu Leu Leu Pro Leu Leu Leu Leu Leu
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic peptide

<400> SEQUENCE: 19

Leu Leu Leu Leu Leu Leu Arg Ala Gln Pro Ala Ile Gly
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic peptide

<400> SEQUENCE: 20

Pro Leu Pro Leu Leu Leu Pro Leu Ser Leu Leu Leu Leu
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic peptide

<400> SEQUENCE: 21

Leu Ser Leu Leu Leu Leu Arg Ala Gln Leu Ala Val Gly
1               5                   10

<210> SEQ ID NO 22
<211> LENGTH: 14
<212> TYPE: PRT
<213> ORGANISM: Artificial sequence
<220> FEATURE:
<223> OTHER INFORMATION: Synthetic peptide

<400> SEQUENCE: 22

Met Leu Pro Gly Leu Ala Leu Leu Leu Leu Ala Ala Trp Thr
1               5                   10

<210> SEQ ID NO 23
<211> LENGTH: 15
<212> TYPE: PRT
<213> ORGANISM: Artificial sequence
<220> FEATURE:
<223> OTHER INFORMATION: Synthetic peptide

<400> SEQUENCE: 23

Pro Gly Leu Ala Leu Leu Leu Leu Ala Ala Trp Thr Ala Arg Ala
1               5                   10                  15

<210> SEQ ID NO 24
<211> LENGTH: 14
<212> TYPE: PRT
<213> ORGANISM: Artificial sequence

```
<220> FEATURE:
<223> OTHER INFORMATION: Synthetic peptide

<400> SEQUENCE: 24

Met Leu Pro Ser Leu Ala Leu Leu Leu Ala Ala Trp Thr
1               5                   10

<210> SEQ ID NO 25
<211> LENGTH: 15
<212> TYPE: PRT
<213> ORGANISM: Artificial sequence
<220> FEATURE:
<223> OTHER INFORMATION: Synthetic peptide

<400> SEQUENCE: 25

Pro Ser Leu Ala Leu Leu Leu Ala Ala Trp Thr Val Arg Ala
1               5                   10                  15

<210> SEQ ID NO 26
<211> LENGTH: 27
<212> TYPE: PRT
<213> ORGANISM: Artificial sequence
<220> FEATURE:
<223> OTHER INFORMATION: Synthetic peptide

<400> SEQUENCE: 26

Leu Leu Leu Leu Leu Leu Val Gly Leu Thr Ala Pro Ala Gly Lys Lys
1               5                   10                  15

Arg Thr Leu Arg Lys Asn Asp Arg Lys Lys Arg
                20                  25
```

METHOD FOR PRODUCING MYOCARDIAL CELLS USING SYNTHETIC PEPTIDE

CROSS REFERENCE TO RELATED APPLICATIONS

This application is a National Stage of International Application No. PCT/JP2016/063411 filed on Apr. 28, 2016, which claims priority to Japanese Application No. 2015-092087 filed on Apr. 28, 2015, the contents of which are hereby incorporated by reference in their entirety.

TECHNICAL FIELD

The present invention relates to a method for producing myocardial cells by inducing the differentiation of pluripotent stem cells into myocardial cells and also relates to a synthetic peptide used in this method.

The present application claims priority based on Japanese Patent Application No. 2015-092087 filed Apr. 28, 2015, and the contents of this Japanese application are incorporated in their entirety in this Description by reference.

BACKGROUND ART

One issue in the field of regenerative medicine is the establishment of technology for the high-efficiency induction of the differentiation of undifferentiated pluripotent stem cells, e.g., embryonic stem cells (also referred to as ES cells) and induced pluripotent stem cells (also referred to as iPS cells), into cells having a desired functionality (refer to Patent Literature 1 to 3 and Non Patent Literature 1 and 2 below). For example, the technology for inducing the differentiation into myocardial cells from cultured iPS cells is described in Patent Literature 3. There are also many reports of methods for inducing the differentiation of undifferentiated pluripotent stem cells into myocardial cells, blood cells, germ cells, nerve cells, and so forth.

In particular, there has been strong demand in recent years for the establishment of technology for the high-efficiency induction of the differentiation of undifferentiated pluripotent stem cells into myocardial cells.

Myocardial cells undergo almost no cell division and it is thus difficult, when myocardial cells have been depleted due to an injury such as myocardial infarction, myocarditis, and cardiomyopathy to restore cardiac function through the regeneration of the damaged tissue via proliferation of the remaining myocardial cells. As a consequence, there is demand for the establishment of technology whereby, for example, undifferentiated pluripotent stem cells can be induced to differentiate into myocardial cells by a highly efficient and simple procedure and the myocardial cells provided by this induced differentiation are supplied to the affected region in place of the lost myocardial cells. The introduction of myocardial cells that can contribute to regenerative medicine is expected to support the treatment of heart diseases as represented by heart failure and ischemic heart disease.

In a typical example of methods known for inducing the differentiation of human pluripotent stem cells to myocardial cells, culture is carried out while supplying the pluripotent stem cells with activin A, which is a peptide having approximately 140 amino acid residues; supply is carried out at any stage during the process of culturing the pluripotent stem cells. In a typical example of methods known for inducing the differentiation of human pluripotent stem cells into hepatocytes, culture is carried out while supplying this activin A to the pluripotent stem cells, with this supply being carried out at any stage during the process of culturing the pluripotent stem cells.

CITATION LIST

Patent Literature

Patent Literature 1: Japanese Patent Application Laid-open No. 2009-165481
Patent Literature 2: Japanese Patent Application Laid-open No. 2009-215191
Patent Literature 3: WO 2007/126077
Patent Literature 4: WO 2009/093692

Non Patent Literature

Non Patent Literature 1: Cell Research, Volume 19, 2009, pp. 1233-1242 Non Patent Literature 2: PLOS ONE, Volume 6 (Number 8), 2011, e24228 Non Patent Literature 3: Jun Cai, et. al., "Protocol for directed differentiation of human pluripotent stem cells toward a hepatocyte fate". StemBook, June 2012.
Non Patent Literature 4: Hepatology, Volume 45 (Number 5), 2007, pp. 1229-1239
Non Patent Literature 5: STEM CELLS, Volume 26, 2008, pp. 894-902
Non Patent Literature 6: Hepatology, Volume 51 (Number 1), 2010, pp. 297-305
Non Patent Literature 7: Cell Research, Volume 23 (Number 1), 2013, pp. 157-161
Non Patent Literature 8: Hepatology, Volume 55 (Number 4), 2012, pp. 1193-1203

SUMMARY OF INVENTION

To date there have been several reports of methods for inducing the differentiation of undifferentiated pluripotent stem cells to myocardial cells. However, existing methods for producing myocardial cells have several problems that prevent the production of myocardial cells that can be used in actual regenerative medical treatments, i.e., an extended amount of time is required to induce the differentiation of myocardial cells, the efficiency of differentiation into myocardial cells is low, the functionality of the differentiation-induced myocardial cells is inadequate (low degree of maturation), and the costs are high because expensive humoral factors, e.g., cytokines, are required in large amounts.

Thus, an object of the present invention is to provide a method for producing myocardial cells by the efficient induction of the differentiation of pluripotent stem cells to myocardial cells. An additional object of the present invention is to provide a composition for producing myocardial cells, the composition being used to produce myocardial cells by the induction of the differentiation of pluripotent stem cells to myocardial cells.

The present inventors surprisingly discovered that the capacity to induce the differentiation of pluripotent stem cells into myocardial cells (this capacity is also referred to below as the "myocardial cell differentiation-inducing activity") is exhibited by peptide synthesized so as to contain an amino acid sequence that is part or all of an amino acid sequence that constitutes the signal peptide (this latter amino acid sequence is also referred to below as the signal peptide sequence) of any protein belonging to the family of amyloid precursor proteins (APP), which are proteins heretofore known for functionalities completely unrelated to the induction of differentiation. The present invention was achieved based on this discovery.

Here, representative examples of proteins belonging to the APP family are amyloid precursor protein (APP) and two species of amyloid precursor-like proteins (amyloid precursor-like protein 1: APLP1, amyloid precursor-like protein 2: APLP2), which are proteins similar to APP.

The myocardial cell production method provided by the present invention is a method for producing myocardial cells from human pluripotent stem cells in vitro or in vivo, and this method includes preparing a cell culture containing the target pluripotent stem cells, and supplying, to the cell culture, an artificially produced synthetic peptide. The synthetic peptide is a peptide that contains a myocardial cell differentiation-inducing peptide sequence that has an activity that induces the differentiation of human pluripotent stem cells into myocardial cells (this activity is also referred to below as the "myocardial cell differentiation-inducing activity").

The myocardial cell differentiation-inducing peptide sequence is an amino acid sequence selected from the group consisting of (i) an amino acid sequence constituting the signal peptide of any protein belonging to the amyloid precursor protein (APP) family, (ii) a partial amino acid sequence that has consecutive amino acid residues from a portion of the amino acid sequence according to (i), and (iii) a modified amino acid sequence formed by the conservative replacement of 1, 2, or 3 amino acid residues in the amino acid sequence according to (i) or (ii).

In this Description, a synthetic peptide containing a myocardial cell differentiation-inducing peptide sequence (i.e., a synthetic peptide having a myocardial cell differentiation-inducing activity) is also referred to as a "myocardial cell differentiation-inducing synthetic peptide".

Also in this Description, the amino acid sequences constituting the signal peptide of any protein belonging to the APP family and partial amino acid sequences within such signal peptide sequences (i.e., consecutive partial sequences of a portion of such a signal peptide sequence) are also collectively referred to as "APP signal peptide-related sequences".

The present method for producing myocardial cells is a method that produces myocardial cells from pluripotent stem cells using the herein disclosed synthetic peptides.

The proteins belonging to the APP family and the signal peptide sequences of such proteins (i.e., APP signal peptide-related sequences) are all known proteins with functions completely unrelated to the induction of differentiation of myocardial cells, and the ability of the aforementioned myocardial cell differentiation-inducing synthetic peptides to induce the differentiation of pluripotent stem cells to myocardial cells is knowledge newly discovered by the present inventors.

The herein disclosed myocardial cell production method can induce myocardial cells from target pluripotent stem cells by a simple and convenient procedure in which a synthetic peptide containing a myocardial cell differentiation-inducing peptide sequence is supplied to the pluripotent stem cells (typically to the culture medium for these cells).

In a preferred aspect of the herein disclosed myocardial cell production method, the supply of the synthetic peptide to the cell culture containing the pluripotent stem cells is executed using the synthetic peptide in place of activin A in a method for inducing the differentiation of human pluripotent stem cells into hepatocytes using the activin A.

The myocardial cell production method of this aspect is a method that is characteristically executed using the aforementioned myocardial cell differentiation-inducing synthetic peptide in place of the activin A used in the hepatocyte production method that is a heretofore known method for producing hepatocytes from pluripotent stem cells, and is thus an entirely novel myocardial cell production method that is different from previous methods for inducing the differentiation of myocardial cells from pluripotent stem cells.

Myocardial cells can be efficiently produced from pluripotent stem cells by executing the supply of the myocardial cell differentiation-inducing synthetic peptide to the target pluripotent stem cells (typically to the culture of these cells) using the synthetic peptide in place of activin A in the method for inducing the differentiation of human pluripotent stem cells into hepatocytes using the activin A as described above.

In another preferred aspect of the herein disclosed myocardial cell production method, the protein belonging to the amyloid precursor protein family is any of amyloid precursor protein, amyloid precursor-like protein 1, and amyloid precursor-like protein 2.

Amyloid precursor protein, amyloid precursor-like protein 1, and amyloid precursor-like protein 2 are all typical examples of proteins that belong to the APP family. Synthetic peptides having an APP signal peptide-related sequence from these proteins and synthetic peptides having a modified amino acid sequence from these sequences are typical examples of peptides having a myocardial cell differentiation-inducing activity and can be advantageously used in the execution of the present invention.

Another preferred aspect of the herein disclosed myocardial cell production method is characterized in that the myocardial cell differentiation-inducing peptide sequence contained in the myocardial cell differentiation-inducing synthetic peptide is constructed from any of the amino acid sequences given in the following i) to vi).

i) The amino acid sequence of SEQ ID NO:1 as follows:

(SEQ ID NO: 1)
MAATGTAAAAATGRLLLLLLVGLTAPALA;

or, a partial amino acid sequence that is a consecutive amino acid sequence of a portion of the amino acid sequence given by SEQ ID NO:1 and that has at least the amino acid sequence given by SEQ ID NO:16;

or, a modified amino acid sequence formed by the conservative replacement of 1, 2, or 3 amino acid residues in these amino acid sequences.

ii) The amino acid sequence of SEQ ID NO:2 as follows:

(SEQ ID NO: 2)
MAATGTAAAAATGKLLVLLLLGLTAPAAA;

or, a partial amino acid sequence that is a consecutive amino acid sequence of a portion of the amino acid sequence given by SEQ ID NO:2 and that has at least the amino acid sequence given by SEQ ID NO:17;

or, a modified amino acid sequence formed by the conservative replacement of 1, 2, or 3 amino acid residues in these amino acid sequences.

iii) The amino acid sequence of SEQ ID NO:3 as follows:

(SEQ ID NO: 3)
MGPASPAARGLSRRPGQPPLPLLLPLLLLLLRAQPAIG;

or, a partial amino acid sequence that is a consecutive amino acid sequence of a portion of the amino acid sequence given by SEQ ID NO:3 and that has at least the amino acid sequence given by SEQ ID NO:18;

or, a partial amino acid sequence that is a consecutive amino acid sequence of a portion of the amino acid sequence given by SEQ ID NO:3 and that has at least the amino acid sequence given by SEQ ID NO:19;

or, a modified amino acid sequence formed by the conservative replacement of 1, 2, or 3 amino acid residues in these amino acid sequences.

iv) The amino acid sequence of SEQ ID NO:4 as follows:

(SEQ ID NO: 4)
MGPTSPAARGQGRRWRPPLPLLLPLSLLLLRAQLAVG;

or, a partial amino acid sequence that is a consecutive amino acid sequence of a portion of the amino acid sequence given by SEQ ID NO:4 and that has at least the amino acid sequence given by SEQ ID NO:20;

or, a partial amino acid sequence that is a consecutive amino acid sequence of a portion of the amino acid sequence given by SEQ ID NO:4 and that has at least the amino acid sequence given by SEQ ID NO:21;

or, a modified amino acid sequence formed by the conservative replacement of 1, 2, or 3 amino acid residues in these amino acid sequences.

v) The amino acid sequence of SEQ ID NO:5 as follows:

(SEQ ID NO: 5)
MLPGLALLLLAAWTARA;

or, a partial amino acid sequence that is a consecutive amino acid sequence of a portion of the amino acid sequence given by SEQ ID NO:5 and that has at least the amino acid sequence given by SEQ ID NO:22;

or, a partial amino acid sequence that is a consecutive amino acid sequence of a portion of the amino acid sequence given by SEQ ID NO:5 and that has at least the amino acid sequence given by SEQ ID NO:23;

or, a modified amino acid sequence formed by the conservative replacement of 1, 2, or 3 amino acid residues in these amino acid sequences.

vi) The amino acid sequence of SEQ ID NO:6 as follows:

(SEQ ID NO: 6)
MLPSLALLLLAAWTVRA;

or, a partial amino acid sequence that is a consecutive amino acid sequence of a portion of the amino acid sequence given by SEQ ID NO:6 and that has at least the amino acid sequence given by SEQ ID NO:24;

or, a partial amino acid sequence that is a consecutive amino acid sequence of a portion of the amino acid sequence given by SEQ ID NO:6 and that has at least the amino acid sequence given by SEQ ID NO:25;

or, a modified amino acid sequence formed by the conservative replacement of 1, 2, or 3 amino acid residues in these amino acid sequences.

The amino acid sequences disclosed as SEQ ID NOs:1 to 6 are representative examples of the amino acid sequences constituting the signal peptides of proteins belonging to the APP family. In addition, the amino acid sequences given in SEQ ID NOs:1 to 6 and the herein disclosed partial amino acid sequences of these amino acid sequences (partial amino acid sequences having at least the amino acid sequences given in SEQ ID NOs:16 to 25) are representative examples of APP signal peptide-related sequences. Peptides containing these amino acid sequences or containing modified amino acid sequences therefrom are peptides that have a high myocardial cell differentiation-inducing activity and can be advantageously used in the execution of the present invention.

In an advantageous aspect of the present invention, the myocardial cell differentiation-inducing synthetic peptide used in the myocardial cell production method has a membrane-permeable peptide sequence at the N-terminal side or C-terminal side of the amino acid sequence of the myocardial cell differentiation-inducing peptide sequence.

The addition to the target pluripotent stem cell (typically to the culture medium) of the myocardial cell differentiation-inducing synthetic peptide having such a membrane-permeable peptide sequence enables the highly efficient transfer of the myocardial cell differentiation-inducing peptide sequence from the outside (outside the cell membrane) of the pluripotent stem cell into the cell interior.

In an advantageous aspect of the present invention, the myocardial cell differentiation-inducing synthetic peptide used in the myocardial cell production method has the following amino acid sequence as this membrane-permeable peptide sequence:

(SEQ ID NO: 7)
KKRTLRKNDRKKR.

The amino acid sequence disclosed here as SEQ ID NO:7 is a representative example of an amino acid sequence that constitutes a membrane-permeable peptide and can be advantageously used in the execution of the present invention.

The total number of amino acid residues constituting the peptide is not more than 100 in a preferred aspect of the myocardial cell differentiation-inducing synthetic peptide used in the herein disclosed myocardial cell production method. The total number of amino acid residues constituting the myocardial cell differentiation-inducing synthetic peptide is more preferably not more than 50.

A peptide having such a short peptide chain has a high structural stability (for example, resistance to protease) and has excellent handling properties and an excellent storability. Moreover, peptide having such a short peptide chain is easily chemically synthesized and can be produced (acquired) at comparatively low production costs. Thus, the use of such a peptide enables the realization of, for example, reductions in the cost of myocardial cell production and improvements in the myocardial cell production efficiency.

In an advantageous aspect of the present invention, the myocardial cell differentiation-inducing synthetic peptide used in the myocardial cell production method has the following amino acid sequence:

(SEQ ID NO: 26)
LLLLLLVGLTAPAGKKRTLRKNDRKKR.

Such a myocardial cell differentiation-inducing synthetic peptide has a particularly high efficiency with regard to inducing the differentiation of pluripotent stem cells into myocardial cells. More specifically, it has an excellent capacity to induce the differentiation of induced pluripotent stem cells (iPS cells) into myocardial cells. It can therefore be advantageously used in the herein disclosed myocardial cell production method.

In another aspect, the present invention provides a composition for producing myocardial cells that is used to produce myocardial cells in vitro or in vivo by inducing the differentiation of human pluripotent stem cells to myocardial cells. This composition contains any of the herein disclosed myocardial cell differentiation-inducing synthetic peptides.

Myocardial cells can be efficiently produced from human-derived pluripotent stem cells by using this composition for producing myocardial cells.

In addition, the myocardial cell differentiation-inducing synthetic peptide used in this composition for producing myocardial cells can be readily artificially produced because it is a synthetic peptide having a relatively short chain length. For example, it can be readily produced by production by chemical synthesis (or biosynthesis). In addition, this myocardial cell differentiation-inducing peptide is a synthetic peptide that has a relatively simple structure (typically a straight-chain peptide chain) and is thus easy to handle and as a consequence is advantageous as an effective component of the composition for producing myocardial cells.

BRIEF DESCRIPTION OF DRAWINGS

FIG. 2 is a micrograph (image) that examines the status of expression of myocardial cell marker genes in the cells when an embodiment of the herein disclosed myocardial cell production method is applied to iPS cells of human origin. The second and third frames from the top give fluorescent images that show the results of an examination, by the immunofluorescent antibody method using anti-MHC antibody or anti-cTnT antibody, respectively, of the expression of MHC (myosin heavy chain) and cTnT (cardiac Troponin T), which are myocardial cell marker genes. The fourth frame from the top gives an image of nuclear staining by DAPI (4',6-diamidino-2-phenylindole), while an image provided by stacking (merging) these fluorescent images and the nuclear staining image is given at the bottom. The result of the bright-field observation of the same visual field is given at the top. Here, the results for a test section that used a myocardial cell differentiation-inducing synthetic peptide according to an embodiment are given on the left, while the results for a control section, where neither the myocardial cell differentiation-inducing synthetic peptide nor activin A was added, are given on the right.

FIG. 3 is a micrograph (image) for checking the status of expression of myocardial cell marker genes in the cells when an embodiment of the herein disclosed myocardial cell production method is applied to iPS cells of human origin. The second and third frames from the top give fluorescent images that show the results of an examination, by the immunofluorescent antibody method using anti-TM antibody or anti-CX43 antibody, respectively, of the expression of TM (tropomyosin) and CX43 (connexin 43), which are myocardial cell marker genes. The fourth frame from the top gives an image of nuclear staining by DAPI, while an image provided by stacking (merging) these fluorescent images and the nuclear staining image is given at the bottom. The result of the bright-field observation of the same visual field is given at the top. Here, the results for a test section that used a myocardial cell differentiation-inducing synthetic peptide according to an embodiment are given on the left, while the results for a control section, where neither the myocardial cell differentiation-inducing synthetic peptide nor activin A was added, are given on the right.

DESCRIPTION OF EMBODIMENTS

Figure 1:
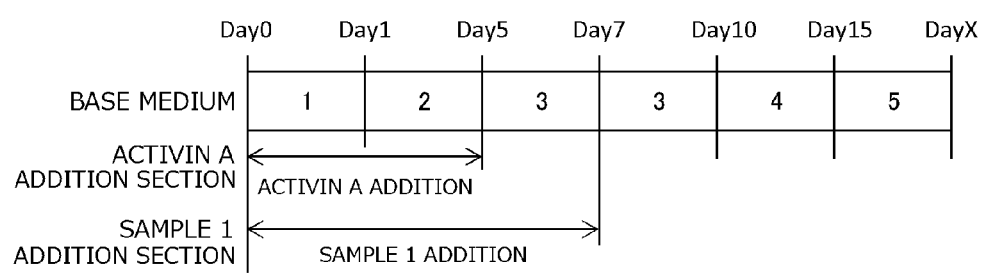
FIG. 1 is a diagram (time chart) that schematically shows the cell culture conditions in an embodiment of the herein disclosed myocardial cell production method.

Preferred embodiments of the present invention are described in the following. In addition to those matters that are particularly described in this Description (for example, the primary structure and chain length of the herein disclosed synthetic peptide), those matters required for the execution of the present invention but not particularly described in this Description (general matters concerning, for example, methods for the chemical synthesis of peptides, cell culture techniques, the preparation of pharmaceutical compositions containing peptides as a component) can be understood as matters of design variation for the person of ordinary skill in the art based on the conventional art in the fields of cell engineering, biophysics, medicine, pharmacology, organic chemistry, biochemistry, genetic engineering, protein engineering, molecular biology, genetics, and so forth. The present invention can be executed based on the contents disclosed in this Description and the common general technical knowledge in the pertinent fields. In the following text, amino acids may be indicated by single-letter designations (three-letter designations in the sequence listings) according to the nomenclature for amino acids set forth in the IUPAC-IUB guidelines.

The entire contents of all the documents cited in this Description are incorporated in this Description by reference.

In the present Description, a "synthetic peptide" is not a peptide chain which by itself independently exists stably in the natural world, but rather refers to a peptide fragment that is produced by artificial chemical synthesis or biosynthesis (i.e., production based on genetic engineering) and is capable of existing stably within a prescribed composition (for example, a composition for producing myocardial cells that is used to produce myocardial cells through the induction of the differentiation of pluripotent stem cells into myocardial cells).

In addition, in the present Description, "peptide" is a term that denotes an amino acid polymer having a plurality of peptide bonds, and, while not being limited by the number of amino acid residues present in the peptide chain, it typically has a relatively low molecular weight with the total number of amino acid residues being approximately 100 or less (preferably not more than 60, for example, not more than 50).

Unless specifically indicated otherwise, in the present Description "amino acid residue" is a term that includes the N-terminal amino acid and the C-terminal amino acid of a peptide chain.

The amino acid sequences described in this Description always assign the N-terminal side to the left side and the C-terminal side to the right side.

In the present Description, a "modified amino acid sequence" refers to an amino acid sequence formed by substituting, deleting, and/or adding (inserting) one or a plurality of amino acid residues, for example, one, two, or three amino acid residues, in, from, and/or to a particular amino acid sequence without a loss in the functionality possessed by the particular amino acid sequence (for example, the myocardial cell differentiation-inducing activity exhibited by a myocardial cell differentiation-inducing synthetic peptide, the membrane permeation capacity exhibited by a membrane-permeable peptide sequence, infra). For example, sequences produced by the maintenance replacement, i.e., the conservative amino acid replacement, of 1, 2, or 3 amino acid residues (for example, a sequence in which a basic amino acid residue has been replaced with another basic amino acid residue: for example, exchanging the lysine residue with the arginine residue), and sequences that arise when 1, 2, or 3 amino acid residues are added to (inserted into) or deleted from a particular amino acid sequence, are typical examples encompassed by the modified amino acid sequences referenced by the present Description. Accordingly, the herein disclosed myocardial cell differentiation-inducing synthetic peptide includes synthetic peptides constituted of the same amino acid sequences as the amino acid sequences with the individual SEQ ID NOs, as well as synthetic peptides comprising an amino acid sequence that is provided by the replacement (for example, the conservative replacement described above), deletion, and/or addition of 1, 2, or 3 amino acid residues in/from/to an amino acid sequence with a particular SEQ ID NO and that exhibits the same myocardial cell differentiation-inducing activity. Amino acid sequences provided by the conservative replacement of 1, 2, or 3 amino acid residues are particularly advantageous as modified amino acid sequences.

In the present Description, "stem cells" refer to cells that have a self-replication capability and are capable of differentiating into 1 or more and preferably 2 or more of various cells, tissue, or organs. In the present Description, stem cells are, for example, ES cells, iPS cells, somatic stem cells (also referred to as tissue stem cells); however, there is no limitation to these as long as the aforementioned capabilities are present.

In the present Description, "pluripotent stem cell" refers to a stem cell that has the capability to differentiate into the various cell types that form a single organism, excluding extra-embryonic tissues such as the placenta, and that also has a self-replication capability in the undifferentiated state. In the present Description, the pluripotent stem cell can be an ES cell or iPS cell, but there is no limitation to these as long as the aforementioned capabilities are present.

In the present Description, "myocardial cell" refers to a cell that has at least one or more of the properties known to be characteristic of myocardial cells. These properties characteristic of myocardial cells include the morphological, structural, and functional characteristics of myocardial cells, or also the state of expression of genes characteristic of myocardial cells (typically that genes characteristic of myocardial cells are being expressed).

For example, myocardial cells beat through a repetitive contraction and relaxation. During contraction the margins of the cell are drawn in towards the center of the cell and the cell assumes a smaller volume. This beat is a spontaneous beat, and beating is repeated autonomously a plurality of times (typically continuously). In an in vitro culture system, myocardial cells can beat even when they are cultured in a state in which the myocardial cells are present independently without contact with surrounding cells. This spontaneous beating is one of the functional characteristics specific to myocardial cells that is not seen in skeletal muscle cells or smooth muscle cells.

In addition, myocardial cells are mononuclear (infrequently binuclear) cells, and the nucleus is located near the center of the cell. This is a morphological characteristic that enables distinction from skeletal muscle, in which the cells are multinuclear and the nuclei are located directly under the cell membrane (typically near the margin of the cell). Furthermore, myocardial cells possess a sarcomere structure in which actin and myosin filaments are regularly aligned (that is, dark and light bands are present). This is a morphological characteristic (a structural characteristic) that enables a distinction to be drawn with smooth muscle cells, which lack this sarcomere structure. Moreover, myocardial cells may also have a branched shape, which is a morphological characteristic that enables distinction from skeletal muscle and smooth muscle.

Myocardial cells can also be distinguished from other cells by the expression of genes characteristic to myocardial cells (typically genes known to be specifically expressed in myocardial cells, i.e., myocardial cell marker genes). The following are typical examples of genes characteristic to myocardial cells: myosin heavy chain (typically α-Myosin Heavy Chain: α-MHC, β-Myosin Heavy Chain: β-MHC), myosin light chain (typically Myosin Light Chain-2a: MLC-2a, Myosin Light Chain-2v: MLC-2v), troponin (typically cardiac Troponin T: cTnT, cardiac Troponin C: cTnC), connexin 43: Cx43, actin (typically α-cardiac Actin), tropomyosin (for example, α-Tropomyosin: α-TM), actinin (typically α-cardiac Actinin), atrial natriuretic peptide (ANP), brain natriuretic peptide (BNP), Nkx2.5 (NK-2 transcription factor related, locus 5), GATA4, and Tbx-5.

Myocardial cells typically do not express genes characteristic of undifferentiated cells (typically pluripotent stem cells).

The herein disclosed myocardial cell production method is a novel method that produces myocardial cells by inducing the differentiation of pluripotent stem cells into myocardial cells in vitro or in vivo. This myocardial cell production method is characterized by supplying at least one of the herein disclosed myocardial cell differentiation-inducing synthetic peptides to pluripotent stem cells (typically in a culture of these cells). An advantageous embodiment encompasses execution using at least one of the herein disclosed myocardial cell differentiation-inducing synthetic peptides in place of activin A in the method for differentiating pluripotent stem cells into hepatocytes using the activin A.

The herein disclosed composition for producing myocardial cells is a composition used to produce myocardial cells by inducing the differentiation of pluripotent stem cells into myocardial cells. In specific terms, this is a composition that characteristically contains, as an effective component (i.e., a substance that contributes to inducing the differentiation of pluripotent stem cells to myocardial cells), at least one of the herein disclosed myocardial cell differentiation-inducing synthetic peptides.

As described in the preceding, the herein disclosed myocardial cell differentiation-inducing synthetic peptide is a synthetic peptide that contains a myocardial cell differentiation-inducing peptide sequence that the present inventors discovered has the ability to differentiate pluripotent stem cells into myocardial cells (i.e., has a myocardial cell differentiation-inducing activity) when supplied to the pluripotent stem cells (typically into the culture medium on which the cells are being cultured). In addition, this myocardial cell differentiation-inducing peptide sequence, when used in place of activin A in the method for inducing the differentiation of human pluripotent stem cells into hepatocytes using activin A, is a sequence confirmed by the present inventors to be an amino acid sequence that can efficiently induce the differentiation of pluripotent stem cells into myocardial cells.

This myocardial cell differentiation-inducing peptide sequence in the herein disclosed myocardial cell differentiation-inducing synthetic peptide is selected from the signal peptide sequences of any protein belonging to the APP family or partial amino acid sequences of these signal peptide sequences (i.e., APP signal peptide-related sequences), or from modified amino acid sequences from these amino acid sequences.

Here, protein belonging to the APP family typically refers to APP, APLP1, or APLP2. In the amyloid hypothesis that is one theory for the pathogenesis of Alzheimer's disease, APP is a protein that should be regarded as a starting substance, so to speak, for Alzheimer's disease, while APLP1 and APLP2 are proteins known as APP-like proteins.

Signal peptide sequences from proteins belonging to the APP family that are preferably used for the execution of the present invention are respectively given by SEQ ID NOs:1 to 6.

Specifically, the amino acid sequence in SEQ ID NO:1 is an amino acid sequence comprising a total of 29 amino acid residues that constitute the signal peptide of APLP2 of human origin.

The amino acid sequence in SEQ ID NO:2 is an amino acid sequence comprising a total of 29 amino acid residues that constitute the signal peptide of APLP2 of mouse origin.

The amino acid sequence in SEQ ID NO:3 is an amino acid sequence comprising a total of 38 amino acid residues that constitute the signal peptide of APLP1 of human origin.

The amino acid sequence in SEQ ID NO:4 is an amino acid sequence comprising a total of 37 amino acid residues that constitute the signal peptide of APLP1 of mouse origin.

The amino acid sequence in SEQ ID NO:5 is an amino acid sequence comprising a total of 17 amino acid residues that constitute the signal peptide of APP of human origin.

The amino acid sequence in SEQ ID NO:6 is an amino acid sequence comprising a total of 17 amino acid residues that constitute the signal peptide of APP of mouse origin.

The amino acid sequences given in SEQ ID NOs:1 to 6 can be used as such as the myocardial cell differentiation-inducing peptide sequence in the construction of the myocardial cell differentiation-inducing synthetic peptide of the present invention.

The signal peptide sequences of human-derived and mouse-derived APP, APLP1, and APLP2 are given in SEQ ID NOs:1 to 6; however, these sequences are nothing more than examples and the utilizable amino acid sequences are not limited thereto. For example, the signal peptide sequences of a variety of APP, APLP1, and APLP2 originating from (typically mammals), e.g., rodents such as the rat and guinea pig, perissodactyls such as the horse and donkey, artiodactyls such as the pig and cow, and primates such as the chimpanzee, orangutan, and cynomolgus monkey, can be used.

Or, a partial amino acid sequence that has consecutive amino acid residues from a portion of the signal peptide sequence of a protein belonging to the APP family (such a partial amino acid sequence is also referred to in the following simply as a partial amino acid sequence) can be used as the myocardial cell differentiation-inducing peptide sequence. For example, a partial amino acid sequence having at least an amino acid sequence as given in SEQ ID NOs:16 to 25 can be advantageously used as the myocardial cell differentiation-inducing peptide sequence in the execution of the present invention.

In the present Description, this "having at least" means having prescribed consecutive amino acid residues (typically any of the amino acid residues shown in SEQ ID NOs:16 to 25) as the required amino acid sequence with the amino acid sequence on the C-terminal side and the amino acid sequence on the N-terminal side from this being optional. That is, the aforementioned partial amino acid sequence can be an amino acid sequence additionally having 1, 2, 3, 4, . . . , or $X_C$ amino acid residues at the C-terminal of prescribed consecutive amino acid residues (typically the amino acid residues given in SEQ ID NOs:16 to 25) and/or 1, 2, 3, 4, . . . , or $X_N$ amino acid residues at the N-terminal thereof. The $X_C$-th amino acid residue on the C-terminal side refers to the C-terminal amino acid residue of the total length of the signal peptide sequence. The $X_N$-th amino acid residue on the N-terminal side refers to the N-terminal amino acid residue of the total length of the signal peptide sequence.

The amino acid sequences given in SEQ ID NOs:16 to 25 are specifically as described in the following.

Thus, the amino acid sequence given in SEQ ID NO:16 is a partial amino acid sequence from the amino acid sequence given in SEQ ID NO:1 and, counting from the amino acid residue at the N-terminal of said amino acid sequence, is an amino acid sequence comprising the 13 consecutive amino acid residues from the leucine residue at position 15 to the alanine residue at position 27.

The amino acid sequence given in SEQ ID NO:17 is a partial amino acid sequence from the amino acid sequence given in SEQ ID NO:2 and, counting from the amino acid residue at the N-terminal of said amino acid sequence, is an amino acid sequence comprising the 12 consecutive amino acid residues from the leucine residue at position 16 to the alanine residue at position 27.

The amino acid sequence given in SEQ ID NO:18 is a partial amino acid sequence from the amino acid sequence given in SEQ ID NO:3 and, counting from the amino acid residue at the N-terminal of said amino acid sequence, is an amino acid sequence comprising the 13 consecutive amino acid residues from the proline residue at position 19 to the leucine residue at position 31.

The amino acid sequence given in SEQ ID NO:19 is a partial amino acid sequence from the amino acid sequence given in SEQ ID NO:3 and, counting from the amino acid residue at the N-terminal of said amino acid sequence, is an amino acid sequence comprising the 13 consecutive amino acid residues from the leucine residue at position 26 to the glycine residue at position 38.

The amino acid sequence given in SEQ ID NO:20 is a partial amino acid sequence from the amino acid sequence given in SEQ ID NO:4 and, counting from the amino acid residue at the N-terminal of said amino acid sequence, is an amino acid sequence comprising the 13 consecutive amino acid residues from the proline residue at position 18 to the leucine residue at position 30.

The amino acid sequence given in SEQ ID NO:21 is a partial amino acid sequence from the amino acid sequence given in SEQ ID NO:4 and, counting from the amino acid residue at the N-terminal of said amino acid sequence, is an amino acid sequence comprising the 13 consecutive amino acid residues from the leucine residue at position 25 to the glycine residue at position 37.

The amino acid sequence given in SEQ ID NO:22 is a partial amino acid sequence from the amino acid sequence given in SEQ ID NO:5 and, counting from the amino acid residue at the N-terminal of said amino acid sequence, is an amino acid sequence comprising the 14 consecutive amino acid residues from the methionine residue at position 1 to the threonine residue at position 14.

The amino acid sequence given in SEQ ID NO:23 is a partial amino acid sequence from the amino acid sequence given in SEQ ID NO:5 and, counting from the amino acid residue at the N-terminal of said amino acid sequence, is an amino acid sequence comprising the 15 consecutive amino acid residues from the proline residue at position 3 to the alanine residue at position 17.

The amino acid sequence given in SEQ ID NO:24 is a partial amino acid sequence from the amino acid sequence given in SEQ ID NO:6 and, counting from the amino acid residue at the N-terminal of said amino acid sequence, is an amino acid sequence comprising the 14 consecutive amino acid residues from the methionine residue at position 1 to the threonine residue at position 14.

The amino acid sequence given in SEQ ID NO:25 is a partial amino acid sequence from the amino acid sequence given in SEQ ID NO:6 and, counting from the amino acid residue at the N-terminal of said amino acid sequence, is an amino acid sequence comprising the 15 consecutive amino acid residues from the proline residue at position 3 to the alanine residue at position 17.

Alternatively, while the herein disclosed myocardial cell differentiation-inducing synthetic peptide may be a peptide composed of only a myocardial cell differentiation-inducing peptide sequence as described in the preceding, it may also be a synthetic peptide having a membrane-permeable peptide sequence at the N-terminal side or C-terminal side of such a myocardial cell differentiation-inducing peptide sequence. With such a synthetic peptide having a membrane-permeable peptide sequence, the synthetic peptide is then able to easily enter into the cells when supplied to the target cells. This can bring about an enhanced myocardial cell differentiation-inducing activity.

Any amino acid sequence constituting a membrane-permeable peptide capable of traversing the cell membrane and/or nuclear membrane can be used without particular limitation as this membrane-permeable peptide sequence. Many suitable membrane-permeable peptide sequences are known; however, an amino acid sequence (including modified amino acid sequences) related to a NoLS (Nucleolar localization signal) is particularly preferred for the amino acid sequence of the membrane-permeable peptide sequence of the myocardial cell differentiation-inducing synthetic peptide. Advantageous examples of NoLS-related membrane-permeable peptide sequences and other membrane-permeable peptide sequences (including modified amino acid sequences) are given in SEQ ID NOs:7 to 15. These are specifically as follows.

Thus, the amino acid sequence in SEQ ID NO:7 corresponds to a NoLS comprising a total of 13 amino acid residues, from the amino acid residue at position 491 to the amino acid residue at position 503, of the LIM Kinase 2 present in human endothelial cells; this is a type of protein kinase that participates in intracellular signal transduction.

The amino acid sequence in SEQ ID NO:8 corresponds to a NoLS comprising a total of 14 amino acid residues originating from FGF2 (basic fibroblast growth factor).

The amino acid sequence in SEQ ID NO:9 corresponds to a NoLS comprising a total of 8 amino acid residues contained in the N protein (nucleocapsid protein) of the IBV (avian infectious bronchitis virus).

The amino acid sequence in SEQ ID NO:10 corresponds to a NoLS comprising a total of 13 amino acid residues originating from the PTP (pre-terminal protein) 1 and PTP2 of adenovirus.

The amino acid sequence in SEQ ID NO:11 corresponds to a membrane-permeable peptide sequence comprising a total of 11 amino acid residues deriving from the protein transduction domain contained in the TAT of HIV (Human Immunodeficiency Virus).

The amino acid sequence in SEQ ID NO:12 corresponds to a membrane-permeable peptide sequence comprising a total of 11 amino acid residues of a protein transduction domain (PTD4) provided by modifying the aforementioned TAT.

The amino acid sequence in SEQ ID NO:13 corresponds to a membrane-permeable peptide sequence comprising a sequence with a total of 16 amino acids deriving from the ANT of Antennapedia, which is a mutant in *Drosophila*.

The amino acid sequence in SEQ ID NO:14 corresponds to a membrane-permeable peptide sequence comprising a total of 9 consecutive arginine residues providing a polyarginine.

The amino acid sequence in SEQ ID NO:15 corresponds to a membrane-permeable peptide sequence comprising a total of 19 amino acid residues derived from MyoD (myoblast determination) family inhibitor domain-containing protein.

These membrane-permeable peptide sequences given in the sequence listings are nothing more than examples, and usable membrane-permeable peptide sequences are not limited to these. A variety of membrane-permeable peptide sequences usable in the execution of the present invention are described in numerous publications that had been published at the time of the filing of the present application. The amino acid sequences of these membrane-permeable peptide sequences can be easily acquired by general search methodologies.

In particular, the amino acid sequence given in SEQ ID NO:7 (and including modified amino acid sequences), which is also described in Patent Literature 4, is preferred for the membrane-permeable peptide sequence. A synthetic peptide exhibiting a high myocardial cell differentiation-inducing performance can be obtained by combining the amino acid sequence in this SEQ ID NO:7 with a myocardial cell differentiation-inducing peptide sequence as described above.

An advantageous embodiment of the herein disclosed myocardial cell differentiation-inducing synthetic peptide contains the following amino acid sequence:

```
                                    (SEQ ID NO: 26)
          LLLLLLVGLTAPAGKKRTLRKNDRKKR.
```

The amino acid sequence given in SEQ ID NO:26 is an amino acid sequence comprising a total of 27 amino acids and constructed by combining, through one glycine residue (G) acting as a linker, the LIM Kinase 2-derived amino acid sequence given in SEQ ID NO:7, with the partial amino acid sequence (SEQ ID NO:16) given in SEQ ID NO:16 from the amino acid sequence (SEQ ID NO:1) constituting the signal peptide of APLP2 of human origin.

Several of the peptide chains (amino acid sequences) of the herein disclosed myocardial cell differentiation-inducing synthetic peptides can be constructed by the suitable combination of a membrane-permeable peptide sequence with a myocardial cell differentiation-inducing peptide sequence as described above. Either of the myocardial cell differentiation-inducing peptide sequence and membrane-permeable peptide sequence may be located at the C-terminal side (or N-terminal side) from the other. The myocardial cell differentiation-inducing peptide sequence and the membrane-permeable peptide sequence are preferably located adjacent to each other. That is, amino acid residues not included in either of the two sequences are preferably not present between the myocardial cell differentiation-inducing peptide sequence and the membrane-permeable peptide sequence, or if present, the number of such residues is preferably about 1 to 3. For example, 1 or several (typically 2 or 3) amino acid residues (for example, 1 or several glycine (G) residues) functioning as a linker may be present between the myocardial cell differentiation-inducing peptide sequence and the membrane-permeable peptide sequence.

Preferably at least one of the amino acid residues in the herein disclosed myocardial cell differentiation-inducing synthetic peptide is amidated. The structural stability of the synthetic peptide (for example, the resistance to proteases) can be improved by the amidation of the carboxyl group in an amino acid residue (typically the C-terminal amino acid residue in the peptide chain).

Insofar as the myocardial cell differentiation-inducing activity is not lost, the myocardial cell differentiation-inducing synthetic peptide may contain a sequence (amino acid residues) portion other than the amino acid sequences constituting the myocardial cell differentiation-inducing peptide sequence and the membrane-permeable peptide sequence. While there are no particular limitations here, this amino acid sequence is preferably a sequence that can maintain the three-dimensional shape (typically the straight-chain shape) of the myocardial cell differentiation-inducing peptide sequence and membrane-permeable peptide sequence portion. The total number of amino acid residues constituting the peptide chain of the myocardial cell differentiation-inducing synthetic peptide is suitably not more than 100, desirably not more than 60, and preferably not more than 50. A synthetic peptide with not more than 30 is particularly preferred.

Such a short-chain length peptide is easily chemically synthesized and the myocardial cell differentiation-inducing synthetic peptide can then be easily produced. There are no particular limitations on the conformation (spatial structure) of the peptide as long as the myocardial cell differentiation-inducing activity, i.e., the induction of the differentiation of pluripotent stem cells to myocardial cells, is exhibited in the use environment (in vitro and typically in the culture medium on which the target cells are cultured); however, a straight-chain or helical shape is preferred from the standpoint of restraining conversion into an immunogen (antigen). It is difficult for a peptide with such a shape to constitute an epitope. Viewed from this perspective, a straight chain shape is preferred for the myocardial cell differentiation-inducing synthetic peptide used in the myocardial cell production method (or the myocardial cell differentiation-inducing synthetic peptide used in the composition for myocardial cell production). Moreover, a relatively low molecular weight (number of amino acid residues of typically not more than 60 (particularly not more than 30)) is advantageous.

The proportion taken up by the myocardial cell differentiation-inducing peptide sequence and membrane-permeable peptide sequence in the overall amino acid sequence (i.e., the number %, with respect to the total number of amino acid residues constituting the peptide chain, for the number of the amino acid residues constituting the myocardial cell differentiation-inducing peptide sequence and membrane-permeable peptide sequence) is not particularly limited as long as the myocardial cell differentiation-inducing activity, i.e., the induction of the differentiation of pluripotent stem cells to myocardial cells, is not lost; however, this proportion is desirably about at least 60%, preferably at least 80%, and particularly preferably at least 90%. In an advantageous embodiment, the peptide is composed of the myocardial cell differentiation-inducing peptide sequence and membrane-permeable peptide sequence (i.e., these sequences account for 100% of the overall amino acid sequence).

Preferably all of the amino acid residues in the myocardial cell differentiation-inducing synthetic peptide according to the present invention are L-amino acids; however, as long as the myocardial cell differentiation-inducing activity, i.e., the induction of the differentiation of pluripotent stem cells to myocardial cells, is not lost, part or all of the amino acid residues may be replaced by D-amino acids.

The herein disclosed myocardial cell differentiation-inducing synthetic peptide can be readily produced by general techniques in chemical synthesis. For example, either a heretofore known solid-phase synthesis method or liquid-phase synthesis method may be adopted. A solid-phase synthesis method that uses Boc (t-butyloxycarbonyl) or Fmoc (9-fluorenylmethyloxycarbonyl) as the protecting group for the amino group is advantageous.

A peptide chain having a desired amino acid sequence and a modified (e.g., C-terminal amidation) portion can be synthesized for the herein disclosed myocardial cell differentiation-inducing synthetic peptide using a solid-phase synthesis procedure using a commercial peptide synthesizer (for example, as can be acquired from e.g., Intavis AG or Protein Technologies, Inc.).

Or, the myocardial cell differentiation-inducing synthetic peptide may be biosynthesized based on a genetic engineering technique. That is, a polynucleotide (typically DNA) is synthesized that has a nucleotide sequence (including the ATG start codon) that codes for the amino acid sequence of the desired myocardial cell differentiation-inducing synthetic peptide. A recombinant vector adapted to the host cell is constructed, wherein this recombinant vector has an expressible gene construct comprising the synthesized polynucleotide (DNA) and the various regulatory elements (including a promoter, ribosome binding site, terminator, enhancer, and various cis elements that control the level of expression) for expression of the amino acid sequence within the host cell.

Using common techniques, this recombinant vector is introduced into a prescribed host cell (for example, yeast, an insect cell, a plant cell) and the host cell or tissue or an individual containing this cell is then cultured under prescribed conditions. Doing this brings about the expression and production of the target peptide in the cell. The peptide is isolated from the host cell (culture medium in the case of secretion), and the target differentiation-inducing synthetic peptide can be obtained by carrying out, e.g., refolding, purification, and so forth, as necessary.

Those methods heretofore performed in this field can be used as such for the method for constructing the recombinant vector, the method for introducing the constructed recombinant vector into the host cell, and so forth, and a detailed description thereof has been omitted since these methods as such are not particular characteristic features of the present invention.

For example, a fusion protein expression system may be employed to efficiently produce large amounts within the host cell. Thus, a gene (DNA) coding for the amino acid sequence of the target myocardial cell differentiation-inducing synthetic peptide is chemically synthesized, and the synthesized gene is inserted at a suitable site in an appropriate fusion protein expression vector (for example, a GST (Glutathione S-transferase) fusion protein expression vector, such as the pET series available from Novagen and the pGEX series available from Amersham Bioscience). The host cells (typically, *Escherichia coli*) are then transformed by the vector. The resulting transformant is cultured, thereby producing the target fusion protein. This protein is then extracted and purified. The resulting purified fusion protein is then digested with a prescribed enzyme (protease), and the liberated target peptide fragments (the designed differentiation-inducing synthetic peptide) are recovered by a method such as affinity chromatography. Refolding is carried out by a suitable method as necessary. The herein disclosed myocardial cell differentiation-inducing synthetic peptide can be produced using such a heretofore known fusion protein expression system (e.g., the GST/His system available from Amersham Bioscience may be used).

Alternatively, the target polypeptide can be synthesized in vitro by constructing template DNA (i.e., a synthesized gene fragment containing a nucleotide sequence that codes for the amino acid sequence of the differentiation-inducing peptide) for a cell-free protein synthesis system and using a so-called cell-free protein synthesis system using the various compounds required for peptide synthesis (e.g., ATP, RNA polymerase, amino acids). For information concerning cell-free protein synthesis systems, reference may be made to, for example, the report by Shimizu et al. (Shimizu et al., Nature Biotechnology, 19, 751-755 (2001)) and the report by Madin (Madin et al., Proc. Natl. Acad. Sci. USA, 97(2), 559-564 (2000)). Based on the technology described in these reports, numerous enterprises were already carrying out the contract production of polypeptides at the time this application was filed. Cell-free protein synthesis kits are also commercially available (for example, the PROTEIOS (trademark) wheat germ cell-free protein synthesis kit available from CellFree Sciences Co., Ltd. (Japan)).

The single-strand or double-strand polynucleotide containing the nucleotide sequence coding for the herein disclosed myocardial cell differentiation-inducing synthetic peptide and/or containing the nucleotide sequence complementary to this sequence, can be easily produced (synthesized) by heretofore known methods. Thus, the nucleotide sequence corresponding to the amino acid sequence of the myocardial cell differentiation-inducing synthetic peptide may be readily determined and provided by selecting the codons that correspond to the individual amino acid residues that constitute the designed amino acid sequence. Once the nucleotide sequence has been determined, the polynucleotide (single strand) corresponding to the desired nucleotide sequence can be easily obtained using, for example, a DNA synthesizer. Using the obtained single-strand DNA as a template, the target double-strand DNA can be obtained using various enzymatic synthesis means (typically PCR). The polynucleotide may take the form of DNA or RNA (e.g., mRNA). The DNA can be provided as the double strand or single strand. When provided as the single strand, it may be the coding strand (sense strand) or may be the noncoding strand (antisense strand) with the sequence complementary thereto.

The thusly obtained polynucleotide can be used as a starting material for the construction of a recombinant gene (expression cassette) for producing the differentiation-inducing synthetic peptide, as described above, in various host cells or using a cell-free protein synthesis system.

The herein disclosed myocardial cell differentiation-inducing synthetic peptide may take the form of a salt provided this does not impair its myocardial cell differentiation-inducing activity. For example, use can be made of the acid-addition salt of the peptide, which can be obtained by an addition reaction with a commonly used inorganic acid or organic acid in accordance with the usual procedures. Or, another salt (for example, a metal salt) may be used as long as the myocardial cell differentiation-inducing activity is retained. Accordingly, the "peptide" referenced in this Description and in the claims includes this salt form.

The herein disclosed composition for producing myocardial cells may contain, in correspondence to the mode of use, various pharmaceutically (medically) acceptable carriers, provided that the myocardial cell differentiation-inducing synthetic peptide that is an active ingredient can be maintained in a state in which its myocardial cell differentiation-inducing activity is not lost. Carriers that are generally used in peptide medications as diluents, excipients, and so forth are preferred. While these may differ as appropriate according to the use and form of the composition for producing myocardial cells, typical examples include water, physiological buffers, and various organic solvents. The carrier may be an aqueous solution containing a suitable concentration of an alcohol (e.g., ethanol), glycerol, or a non-drying oil such as olive oil. Alternatively, the carrier may be liposomes. Secondary ingredients that may be included in the composition for producing myocardial cells can be exemplified by various fillers, thickeners, binders, wetting agents, surfactants, colorants, fragrances, and so forth.

The form of the composition for producing myocardial cells is not particularly limited. Examples of typical forms include liquid preparations, suspensions, emulsions, aerosols, foams, pellets, powders, tablets, capsules, ointments, aqueous gels, and so forth. The composition for producing myocardial cells may also be made into a freeze-dried form or granules for preparing a drug solution by dissolution in, for example, physiological saline or a suitable buffer (e.g., phosphate-buffered saline (PBS)), immediately prior to use.

The process of preparing a drug (composition) in various forms by using the myocardial cell differentiation-inducing synthetic peptide (main ingredient) and various carriers (secondary ingredients) as starting materials may itself be in accordance with heretofore known methods, and a detailed description thereof is omitted because such formulation methods are not themselves characteristic features of the present invention. An example of a detailed information source relating to formulation is Comprehensive Medicinal Chemistry, edited by Corwin Hansch and published by Pergamon Press (1990). The entire contents of this work are incorporated in this Description by reference.

There are no particular limitations on the pluripotent stem cells that are the target for the application of the herein disclosed myocardial cell differentiation-inducing synthetic peptide (i.e., the composition for producing myocardial cells that contains this peptide), i.e., the pluripotent stem cells that are the target for the application of the myocardial cell production method, and a variety of pluripotent stem cells can be induced to differentiate into myocardial cells (or the induction of their differentiation can be promoted). Examples are iPS cells and ES cells of human origin. iPS cells are more easily acquired than ES cells. In addition, in comparison to myocardial cells produced from other pluripotent stem cells (for example, ES cells), myocardial cells (and tissue containing these cells) produced from iPS cells can lower the risk of rejection reactions when these myocardial cells are transplanted into an organism. Accordingly, iPS cells of human origin are particularly preferred as the target cells for the application of the herein disclosed myocardial cell differentiation-inducing synthetic peptide.

The herein disclosed myocardial cell differentiation-inducing synthetic peptide can be used by a method and in a dose adapted to its form and its intended purpose.

For example, a suitable amount of the herein disclosed myocardial cell differentiation-inducing synthetic peptide may be added to the culture medium at any stage in the process of culturing (culture (growth) for a prescribed period of time or post-subculture) the pluripotent stem cells (typically a cell culture containing these cells) that are the target for induction. The myocardial cell differentiation-inducing synthetic peptide is typically added to the culture medium in the initial stage (typically the earliest stage) of inducing the differentiation of the pluripotent stem cells into myocardial cells. The amount of addition of the myocardial cell differentiation-inducing synthetic peptide and the number of times for its addition are not particularly limited because these can vary as a function of conditions such as, for example, the type of cultured cell, the cell density (cell density at the start of culture), number of subcultures, culture conditions, and type of culture medium. For example, preferably a single addition or a plurality of additions (for example, at the start of culture with supplementary addition during subculture of the cells and/or during medium exchange) are made so as to bring the concentration of the myocardial cell differentiation-inducing synthetic peptide in the culture medium into the range of about at least 0.1 µM and not more than 100 µM and preferably into the range of at least 0.5 µM and not more than 20 µM (for example, at least 1 µM and not more than 10 µM).

There are no particular limitations on the time period for culturing the target pluripotent stem cells on a culture medium containing the myocardial cell differentiation-inducing synthetic peptide, and culture should be carried out on a culture medium containing the myocardial cell differentiation-inducing synthetic peptide for a period of time sufficient to induce the differentiation of the target pluripotent stem cells to myocardial cells. For example, the target pluripotent stem cells are preferably cultured on a culture medium containing the myocardial cell differentiation-inducing synthetic peptide for at least 3 days (preferably at least 5 days) and not more than 10 days (preferably not more than 7 days).

When the herein disclosed myocardial cell production method is executed, the presence of myocardial cells can be confirmed after about the 9th day (typically after about 11 days) after starting the induction of differentiation to myocardial cells (typically after the addition of the myocardial cell differentiation-inducing synthetic peptide). With regard to the presence of these myocardial cells, more myocardial cells (typically myocardial cells having an autonomous beating capacity) can be confirmed from about 15 days (preferably from 17 days, more preferably from 20 days, and still more preferably from 25 days) after the start of the induction of the differentiation of the pluripotent stem cells to myocardial cells (typically after the addition of the myocardial cell differentiation-inducing synthetic peptide). As a consequence, cell culture is preferably carried out under prescribed conditions for an interval of at least 15 days (preferably at least 17 days, more preferably at least 20 days, and still more preferably at least 25 days) and not more than 50 days (preferably not more than 40 days and more preferably not more than 35 days) after the induction of the differentiation of the pluripotent stem cells to myocardial cells.

In a preferred embodiment, the myocardial cell differentiation-inducing synthetic peptide is supplied to the pluripotent stem cells by using the myocardial cell differentiation-inducing synthetic peptide in place of activin A in the method for inducing the differentiation of human pluripotent stem cells to hepatocytes using the activin A. That is, a preferred embodiment of the herein disclosed myocardial cells encompasses the execution of the method for inducing the differentiation of human pluripotent stem cells to hepatocytes using activin A, using the herein disclosed myocardial cell differentiation-inducing synthetic peptide in place of the activin A. Typically, the pluripotent stem cells are cultured in the presence of the herein disclosed myocardial cell differentiation-inducing synthetic peptide for the same period of time as in the culture of the target pluripotent stem cells in the presence of activin A in the aforementioned method for inducing the differentiation of hepatocytes from pluripotent stem cells using activin A. For example, a suitable amount of the myocardial cell differentiation-inducing synthetic peptide (for example, about at least 0.1 µM and not more than 100 µM as the concentration of the myocardial cell differentiation-inducing synthetic peptide in the culture medium, and preferably at least 0.5 µM and not more than 20 µM, for example, at least 1 µM and not more than 10 µM) is supplied to the target pluripotent stem cells using the same timing as the timing for the supply of the activin A to the pluripotent stem cells in the method for inducing the differentiation of human pluripotent stem cells to hepatocytes using activin A.

Activin A and the myocardial cell differentiation-inducing synthetic peptide presumably can have different stabilities in culture media. Due to this, the amount of the myocardial cell differentiation-inducing synthetic peptide supplied to the pluripotent stem cells (typically the amount of addition to the culture medium on which the pluripotent stem cells are cultured) may not be the same as the amount of activin A supplied to the pluripotent stem cells in the method for inducing the differentiation of pluripotent stem cells to hepatocytes using activin A. In addition, the number of times of supply (number of times of addition) of the activin A in the method for inducing the differentiation of pluripotent stem cells to hepatocytes using activin A, may not be the same as the number of times of addition of the myocardial cell differentiation-inducing synthetic peptide in the herein disclosed myocardial cell production method. Thus, the myocardial cell differentiation-inducing synthetic peptide should be supplied to the pluripotent stem cells such that a suitable amount of the myocardial cell differentiation-inducing synthetic peptide is supplied to the pluripotent stem cells (typically addition to the culture medium on which the pluripotent stem cells are cultured) for the time period required to induce the differentiation of the pluripotent stem cells to myocardial cells (typically the time period for which the pluripotent stem cells are cultured in the presence of activin A in the method for inducing the differentiation of hepatocytes from pluripotent stem cells using activin A).

When the supply of the myocardial cell differentiation-inducing synthetic peptide to the pluripotent stem cells is carried out by using the myocardial cell differentiation-inducing synthetic peptide in place of activin A in the method for inducing the differentiation of human pluripotent stem cells into hepatocytes using the activin A, the herein disclosed myocardial cell differentiation-inducing synthetic peptide may be used in place of a portion or all (preferably all) of the activin A using in the indicated method for producing hepatocytes. Co-use with activin A is preferably not employed from the standpoint of the efficiency of inducing the differentiation of pluripotent stem cells into myocardial cells (differentiation induction efficiency).

When the supply of the myocardial cell differentiation-inducing synthetic peptide to the pluripotent stem cells is carried out by using the myocardial cell differentiation-inducing synthetic peptide in place of activin A in the method for inducing the differentiation of human pluripotent stem cells into hepatocytes using the activin A, the period of time for culturing the target pluripotent stem cells in the culture medium containing the myocardial cell differentiation-inducing synthetic peptide may be the same period of time as that for culturing the pluripotent stem cells in the presence of activin A in the method for inducing the differentiation of pluripotent stem cells into hepatocytes using activin A. The culture time in the presence of the myocardial cell differentiation-inducing synthetic peptide may be varied as appropriate as a function of conditions such as the type of the target pluripotent stem cell, the cell density (cell density at the start of culture), the number of subcultures, the culture conditions, and the type of culture medium. For example, the culture time in the presence of the myocardial cell differentiation-inducing synthetic peptide may be changed to be several days (for example 1 day and typically 2 days) longer or shorter than the period of time for culturing the pluripotent stem cells in the presence of activin A in the method for inducing the differentiation of pluripotent stem cells into hepatocytes. For example, the target pluripotent stem cells are preferably cultured in a culture medium containing the myocardial cell differentiation-inducing synthetic peptide for at least 3 days (preferably at least 5 days) and not more than 10 days (preferably not more than 7 days).

The hepatocyte differentiation-inducing method to which the myocardial cell differentiation-inducing synthetic peptide (i.e., a composition for producing myocardial cells that contains this peptide) is applied in the herein disclosed myocardial cell production method, should be a method that uses activin A and is known to be able to induce the differentiation of pluripotent stem cells to hepatocytes, but is not otherwise particularly limited. This hepatocyte differentiation-inducing method can be exemplified by the methods described in Non Patent Literature 3 to Non Patent Literature 8 and methods provided by the partial modification thereof.

The method described in Non Patent Literature 3 contains the following steps (i) to (v).

(i) The pluripotent stem cells are cultured for 2 days on a cell culture medium provided by the addition of activin A, FGF2 (Fibroblast Growth Factor 2), and BMP4 (Bone Morphogenetic Protein 4) to RPMI1640 medium (Roswell Park Memorial Institute medium) containing B27 (registered trademark) Supplement (minus insulin).

(ii) After culture in accordance with (i), culture is carried out for 2 days on a cell culture medium provided by the addition of activin A to RPMI1640 medium containing B27 (registered trademark) Supplement (minus insulin).

(iii) After culture in accordance with (ii), culture is carried out for 5 days on a cell culture medium provided by the addition of BMP4 and FGF2 to RPMI1640 medium containing B27 (registered trademark) Supplement (containing insulin).

(iv) After culture in accordance with (iii), culture is carried out for 5 days on a cell culture medium provided by the addition of HGF (Hepatocyte Growth Factor) to RPMI1640 medium containing B27 (registered trademark) Supplement (containing insulin).

(v) After culture in accordance with (iv), culture is carried out for 5 days on a cell culture medium provided by the addition of OSM (oncostatin M) to HCM medium (minus EGF).

The HCM (registered trademark) medium (Hepatocyte culture Medium) here is available by the purchase of products sold as hepatocyte culture media (e.g., products from Lonza Ltd) (detailed composition not disclosed). This also applies in the following.

The method described in Non Patent Literature 4 contains the following steps (i) to (iv).

(i) The pluripotent stem cells are cultured for 3 days on a cell culture medium provided by the addition of activin A to RPMI1640 medium.

(ii) After culture in accordance with (i), culture is carried out for 5 days on a cell culture medium provided by the addition of FGF4 and BMP2 to the aforementioned HCM medium.

(iii) After culture in accordance with (ii), culture is carried out for 5 days on a cell culture medium provided by the addition of HGF to the aforementioned HCM medium.

(iv) After culture in accordance with (iii), culture is carried out for 5 days on a cell culture medium provided by the addition of OSM and Dex (Dexamethasone) to the aforementioned HCM medium.

The method described in Non Patent Literature 5 contains the following steps (i) to (iii).

(i) The pluripotent stem cells are cultured for 5 days on a cell culture medium provided by the addition of activin A and NaB (sodium butyrate) to RPMI1640 medium containing B27 (registered trademark) Supplement.

(ii) After culture in accordance with (i), culture is carried out for 7 days on a cell culture medium provided by the addition of DMSO (Dimethyl sulfoxide) to KO-DMEM (KnockOut-Dulbecco's modified Eagle's medium) containing KSR (KnockOut (registered trademark) Serum Replacement).

(iii) After culture in accordance with (ii), culture is carried out for 7 days on a cell culture medium provided by the addition of HGF and OSM to L15 medium containing FBS (Fatal Bovine Serum).

The method described in Non Patent Literature 6 contains the following steps (i) to (iv).

(i) The pluripotent stem cells are cultured for 5 days on a cell culture medium provided by the addition of activin A to RPMI1640 medium containing B27 (registered trademark) Supplement.

(ii) After culture in accordance with (i), culture is carried out for 5 days on a cell culture medium provided by the addition of FGF4 and BMP2 to RPMI1640 medium containing B27 (registered trademark) Supplement.

(iii) After culture in accordance with (ii), culture is carried out for 5 days on a cell culture medium provided by the addition of HGF to RPMI1640 medium containing B27 (registered trademark) Supplement.

(iv) After culture in accordance with (iii), culture is carried out for 5 days on a cell culture medium provided by the addition of OSM to the aforementioned HCM medium.

The method described in Non Patent Literature 7 contains the following steps (i) to (v).

(i) The pluripotent stem cells are cultured for 3 days on a cell culture medium provided by the addition of activin A to RPMI1640 medium containing B27 (registered trademark) Supplement.

(ii) After culture in accordance with (i), culture is carried out for 2 days on a cell culture medium provided by the addition of FGF7 and SB431542 (ALK inhibitor) to RPMI1640 medium containing B27 (registered trademark) Supplement.

(iii) After culture in accordance with (ii), culture is carried out for 5 days in a cell culture medium provided by the addition of FGF7, BMP2, and BMP4 to RPMI1640 medium containing B27 (registered trademark) Supplement.

(iv) After culture in accordance with (iii), culture is carried out for 5 days on a cell culture medium provided by the addition of HGF and BMP4 to RPMI1640 medium containing B27 (registered trademark) Supplement.

(v) After culture in accordance with (iv), culture is carried out for 5 days on a cell culture medium provided by the addition of OSM and Dex to the aforementioned HCM.

The method described in Non Patent Literature 8 contains the following steps (i) to (iii).

(i) The pluripotent stem cells are cultured for 4 days on a cell culture medium provided by the addition of activin A, Wnt3a (wingless-type MMTV integration site family, member 3A) and HGF to RPMI1640 medium containing B27 (registered trademark) Supplement.

(ii) After culture in accordance with (i), culture is carried out for 3 days on a cell culture medium provided by the addition of DMSO to KO-DMEM medium containing KSR.

(iii) After culture in accordance with (ii), culture is carried out for 4 days on a cell culture medium provided by the addition of OSM and Dex to IMDM (Iscove's Modified Dulbecco's Medium).

Thus, the herein disclosed myocardial cell production method can be a method in which a hepatocyte differentiation-inducing method described in Non Patent Literature 3 to Non Patent Literature 8 is executed using the herein disclosed myocardial cell differentiation-inducing synthetic peptide in place of the activin A used the latter method.

The herein disclosed myocardial cell differentiation-inducing synthetic peptide can be used as appropriate in combination with other extrinsic factors (for example, cytokines and hormones). Thus, the composition for producing myocardial cells can contain other extrinsic factors (for example, cytokines and hormones) as appropriate as a component in addition to the myocardial cell differentiation-inducing synthetic peptide. Or, the pluripotent stem cells may be cultured on a culture medium to which these other extrinsic factors have been added, this culture being carried out prior to culture of the pluripotent stem cells on a medium containing the herein disclosed myocardial cell differentiation-inducing synthetic peptide or after such a culture.

For example, the myocardial cell differentiation-inducing synthetic peptide can be used in combination with the various extrinsic factors, other than activin A, that are used in the method for inducing the differentiation of pluripotent stem cells into hepatocytes using activin A, or these may be used while shifting the time of addition with respect to the myocardial cell differentiation-inducing synthetic peptide. These extrinsic factors can be exemplified by factors belonging to the FGF superfamily, e.g., FGF1, FGF2, FGF4, FGF7, and so forth; bone morphogenetic factors (factors belonging to the BMP family), e.g., BMP2, BMP4, and so forth; and extrinsic factors, e.g., HGF, OSM, Dex, and so forth.

The myocardial cell differentiation-inducing synthetic peptide may optionally be used in combination with extrinsic factors other than the extrinsic factors used in the method for inducing the differentiation of pluripotent stem cells into hepatocytes using activin A, or these may be used while shifting the time of addition with respect to the myocardial cell differentiation-inducing synthetic peptide. These extrinsic factors can be exemplified by retinoic acid; factors belonging to the TGF-β superfamily, e.g., TGF-β and so forth; so-called growth factors such as leukemia inhibitory factor (LIF), cholinergic differentiation factor (CDF), ciliary neurotrophic factor (CNTF), and EGF; other factors belonging to the cytokine family; various interleukins, tissue necrosis factor (TNF-α), interferon γ (IFNγ), and so forth.

Thus, an embodiment of the herein disclosed myocardial cell production method is a method that uses the combination of the myocardial cell differentiation-inducing synthetic peptide and an extrinsic factor as described above. For example, it can be a myocardial cell production method containing the following steps (i) to (iii).

Thus, an embodiment of the herein disclosed myocardial cell production method is a myocardial cell production method containing the following:

(i) a step of culturing pluripotent stem cells on a cell culture medium to which the myocardial cell differentiation-inducing synthetic peptide, FGF2, and BMP4 have been added;

(ii) a step of culturing the cells provided by (i) on a cell culture medium to which the myocardial cell differentiation-inducing synthetic peptide has been added; and (iii) a step of culturing the cells provided by (ii) on a cell culture medium to which the myocardial cell differentiation-inducing synthetic peptide, BMP4, and FGF2 have been added.

The myocardial cell production method containing these steps (i) to (iii) may additionally contain, after step (iii), at least one step from the following steps (iv) to (vi):

(iv) a step of culturing on a cell culture medium to which BMP4 and FGF2 have been added;

(v) a step of culturing on a cell culture medium to which HGF has been added; and (vi) a step of culturing on a cell culture medium to which oncostatin M has been added.

When two or more of these steps (iv) to (vi) are included, they are carried out in the sequence (iv), (v), (vi).

The common culture media using in the cultivation of human-derived cells can be used without particular limitation as the culture medium used in the herein disclosed myocardial cell production method. Typically the same culture media as the culture media used in the hepatocyte differentiation-inducing method using activin A can be used. Examples are RPMI1640 medium, HCM, DMEM, KO-DMEM, IMDM, Ham's F-12 medium, MEM, α-MEM, GMEM, and so forth. These media may as necessary be combined with the usual additive components that are added to the culture of human-derived cells. These additive components can be exemplified by FBS, KSR, B27 (registered trademark) Supplement, various antibiotics, amino acids, vitamins, and so forth.

The myocardial cells produced using the herein disclosed art are cells that have at least one or more of the properties characteristic of myocardial cells. These properties characteristic of myocardial cells are typically the morphological, structural, and functional characteristics of myocardial cells, or also the state of expression of genes characteristic of myocardial cells (typically that genes characteristic of myocardial cells are being expressed).

In specific terms, these myocardial cells can be cells that engage in repetitive autonomous beating a plurality of times. In addition, these myocardial cells can be mononuclear (infrequently binuclear) cells and can be cells in which this nucleus is located near the center of the cell. Or, these myocardial cells can be cells having a sarcomere structure in which actin and myosin filaments are regularly aligned (that is, dark and light bands are present). Or, these myocardial cells can be cells that are expressing genes characteristic to myocardial cells (typically genes known to be specifically expressed by myocardial cells, i.e., myocardial cell marker genes).

Thus, the myocardial cells produced by the herein disclosed art can be cells that express at least one or more (preferably at least 2, more preferably at least 3, and even more preferably at least 4) of the genes known to be characteristically expressed by myocardial cells (i.e., myocardial cell marker genes), e.g., myosin heavy chain (typically α-Myosin Heavy Chain (α-MHC), β-Myosin Heavy Chain (β-MHC)), myosin light chain (typically Myosin Light Chain-2a (MLC-2a), Myosin Light Chain-2v (MLC-2v)), troponin (typically cardiac Troponin T (cTnT), cardiac Troponin C (cTnC)), connexin 43 (Cx43), actin (typically α-cardiac Actin), tropomyosin (typically α-Tropomyosin (α-TM)), actinin (typically α-cardiac Actinin), atrial natriuretic peptide (ANP), brain natriuretic peptide (BNP), NkX2.5 (NK-2 transcription factor related, locus 5), GATA4, Tbx-5, and so forth. Among these, α-Myosin Heavy Chain (α-MHC), β-Myosin Heavy Chain (β-MHC), Myosin Light Chain-2a (MLC-2a), Myosin Light Chain-2v (MLC-2v), cardiac Troponin T (cTnT), cardiac Troponin C (cTnC), connexin 43 (Cx43), α-cardiac Actin, α-cardiac Actinin, atrial natriuretic peptide (ANP), brain natriuretic peptide (BNP), and NkX2.5 (NK-2 transcription factor related, locus 5), being genes that are specifically expressed by myocardial cells, are preferred as myocardial cell marker genes for determining whether the obtained cells are myocardial cells.

Thus, that the cells obtained by the herein disclosed method are myocardial cells can be ascertained by checking, using an appropriate method, for the presence of at least one of the aforementioned properties that are characteristic of myocardial cells. For example, whether the cells engage in the repetitive autonomous beating referenced above can be checked by microscopic observation (typically observation using an optical microscope, bright-field observation, and so forth). The presence of a cellular feature characteristic of myocardial cells (mononuclear cells, presence of sarcomere structure, and so forth) can be checked by the microscopic observation of the cells stained with a cytostain using a special dye, an immunostain that uses an antigen-antibody reaction (antibody stain, immunoantibody method), and so forth. The expression of a gene specific to myocardial cells can be checked using heretofore known methods to check for the presence of mRNA or protein that is the gene product. The mRNA can be confirmed by, for example, the PCR method (preferably RT-PCR), and the protein can be confirmed, for example, by methods that use an immunological procedure (for example, cytoimmunostaining, Western blotting, and flow cytometry).

The myocardial cells produced by the herein disclosed art can be present in the form of cell aggregates (clusters, colonies) formed by the assembly (aggregation) of a plurality of cells containing the myocardial cells. This cell aggregate (cluster) typically contains a plurality of cells (myocardial cells) that engage in repetitive synchronous beating, and preferably can contain a plurality of cells (myocardial cells) that are electrically linked with one another. The electrical linkage between these cells can preferably be a linkage by gap junctions.

The herein disclosed myocardial cell production method may additionally include the sorting (separation) of the cells that have differentiated into myocardial cells (or clusters containing these myocardial cells), from the cell culture provided by culturing while being provided with the myocardial cell differentiation-inducing synthetic peptide. By recovering these sorted (separated) myocardial cells, it is then possible to produce a myocardial cell population (cell culture containing this cell population) that has a high proportion (purity) of myocardial cells in the total cells.

Thus, the herein disclosed myocardial cell production method can include a sorting (separation) of the myocardial cells from the cell culture containing the myocardial cells, using a property characteristic of myocardial cells (marker, label, benchmark) as the indicator. This property characteristic of myocardial cells should be a property that enables the discrimination of myocardial cells from non-myocardial cells expected to be present in the cell culture, but is not otherwise particularly limited. For example, the following can be used as the property (characteristic) of the myocardial cells employed to sort the myocardial cells from a target cell culture: functional characteristics, morphological characteristics, or structural characteristics of myocardial cells, or the state of expression of genes characteristic of myocardial cells (typically genes that are specifically expressed by myocardial cells, i.e., myocardial cell marker genes), or physiological characteristics (growth properties, adherence properties, migration behavior, cell division features, nutritional requirements, and so forth) that are characteristic of myocardial cells. For example, the same properties as described above can be advantageously utilized as the properties characteristic of myocardial cells that can be used to check whether the cells provided by the herein disclosed myocardial cell production method are myocardial cells.

With regard to methods for sorting (separating) the myocardial cells from a myocardial cell-containing cell culture, sorting of the myocardial cells and recovery of the myocardial cells can be carried out by, for example, the use of a suitable selection medium; harvesting (picking up), under a microscope, cells that have the functional characteristics (for example, beating cells) or the morphological (structural) characteristics of myocardial cells; carrying out cell sorting (for example, cell sorting using a FACS (fluorescence-activated cell sorter) or a magnetic cell separator (for example, a MACS (magnetic cell sorter))) based on the state of expression of a myocardial cell marker gene (typically the presence of protein or mRNA that is a gene product of such a gene); and carrying out cell sorting using a physiological property characteristic of myocardial cells (growth properties, adherence properties, migration behavior, cell division features, nutritional requirements). These sorting methods are examples of methods for sorting the myocardial cells from a cell culture and there is no limitation to these. For example, various methods that recover specific cells from a culture medium can be adopted. In addition, a single one of these myocardial cell sorting methods may be implemented by itself or a combination of two or more of these methods may be carried out.

Alternatively, pluripotent stem cells that have not undergone differentiation into myocardial cells will presumably be present as non-myocardial cells in the myocardial cell-containing cell culture in the herein disclosed myocardial cell production method. Due to this, for example, the pluripotent stem cells may be removed from the myocardial cell-containing cell culture using a property (marker, label, benchmark) characteristic of pluripotent stem cells as the indicator. While the description here has used the presence of pluripotent stem cells in the myocardial cell-containing cell culture as an example, there is no limitation to this. For example, when insufficiently differentiated cells, endodermal cells, ectodermal cells, muscle cells other than the myocardium, such as skeletal muscle or smooth muscle, and so forth are present in the cell culture, these cells can be removed from the myocardial cell-containing cell culture using properties characteristic of the particular cells.

The herein disclosed myocardial cell production method can efficiently produce myocardial cells (or tissue or an organ containing these cells) from pluripotent stem cells (for example, iPS cells or ES cells) that cultured (subcultured) in vitro. In particular, the herein disclosed myocardial cell production method can produce myocardial cells that exhibit a high myocardial cell functionality (typically cells that engage in repetitive autonomous beating). In addition, the myocardial cells can be produced at better efficiencies (higher differentiation induction efficiency, e.g., higher production efficiency) than in conventional methods for producing myocardial cells from pluripotent stem cells. In other words, a cell culture having a high proportion of myocardial cells in the overall cell population can be acquired.

Repair or regeneration can be effectively performed by returning the myocardial cells (or tissue or organ containing these cells) efficiently produced in vitro by the herein disclosed myocardial cell production method, to an affected part requiring repair or regeneration (i.e., within the body of a patient). An efficient treatment becomes possible for various diseases for which tissue regeneration is an effective therapy. In addition, the myocardial cells produced in vitro by the herein disclosed production method can be used, for example, as a medical material that contributes to the treatment, by a regenerative medical approach, of diseases in which myocardial cells are damaged, e.g., myocardial infarction, myocarditis, cardiomyopathy, and so forth, or damage to such tissue.

Otherwise, myocardial cells produced in large amounts in vitro (in vitro culture system) contribute to evaluating the toxicity and efficacy of drug products, and this enables the realization of lower costs and an improved efficiency and accuracy for such evaluations. Specifically, the myocardial cells provided by the herein disclosed myocardial cell production method can be advantageously applied to the pharmacological activity testing and toxicity testing of drugs. The use of myocardial cells of human origin can contribute to the development of drugs useful (more effective, safer) for the treatment of humans. Moreover, the costs of drug development can be lowered through the use of cells that have been efficiently cultured on a large scale in an in vitro culture system. The use of myocardial cells produced in large amounts in vitro (in vitro culture system) enables the production of biosynthetic products originating from these cells, and specifically physiologically active substances such as secreted proteins and hormones (for example, ANP: Atrial natriuretic factor, BNP: brain natriuretic factor, FSTL1: Follistatin-like 1).

In addition, the use of myocardial cells produced in large amounts in vitro (in vitro culture system) as the test substrate enables the execution of tests where interpretation has previously been problematic. For example, in fields such as the elucidation of disease pathologies and therapeutic drug research and development, research can be efficiently carried out through the utilization of myocardial cells produced from pluripotent stem cells of human origin.

Several examples of the present invention are described below, but this should not be taken to mean that the present invention is limited to or by that which is shown in these examples.

Example 1: Peptide Synthesis

A synthetic peptide comprising the amino acid sequence given in SEQ ID NO:26 was produced using the peptide synthesizer described below. This synthetic peptide is designated sample 1 in the description that follows. The carboxyl group (—COOH) on the C-terminal amino acid in this synthetic peptide is amidated (—CONH$_2$).

The sample 1 peptide was synthesized by a solid-phase synthesis method (Fmoc method) in accordance with the manual using a commercial peptide synthesizer (Intavis AG). The mode of use of the peptide synthesizer is itself not a characteristic feature of the present invention and its detail description has therefore been omitted.

The synthesized peptide was dissolved in a solvent prepared by mixing 1 volume of DMSO with 1 volume of ethanol (DMSO/EtOH=1/1) to prepare a stock solution.

Example 2: Production of Myocardial Cells

Pluripotent stem cells were induced to myocardial cells (production of myocardial cells) using the myocardial cell differentiation-inducing synthetic peptide obtained in Example 1 (sample 1). Specifically, pluripotent stem cells were induced to myocardial cells (production of myocardial cells) by using the myocardial cell differentiation-inducing synthetic peptide obtained in Example 1 (sample 1) in place of activin A in the method for inducing the differentiation of pluripotent stem cells into hepatocytes. The method described in Non Patent Literature 3 was adopted for the method for inducing the differentiation of pluripotent stem cells into hepatocytes. iPS cells of human origin (clone designation: 201B7, source: Takahashi K et al., Cell, 131, 861-872 (2007)) were used for the test cells. These iPS cells were supplied by the Center for iPS Cell Research and Application of Kyoto University.

Culture media with the compositions given below were first prepared for use in the production of myocardial cells from pluripotent stem cells using the myocardial cell differentiation-inducing synthetic peptide obtained in Example 1 (sample 1). These media with the indicated compositions are designated base media 1 to 5.

Base medium 1 is a culture medium containing 2 volume % B27 (registered trademark) Supplement (minus insulin), 10 ng/mL of BMP4, and 20 ng/mL of FGF2 in RPMI1640 culture medium.

Base medium 2 is a culture medium containing 2 volume % B27 (registered trademark) Supplement (minus insulin) in RPMI1640 culture medium.

Base medium 3 is a culture medium containing 2 volume % B27 (registered trademark) Supplement, 20 ng/mL of BMP4, and 10 ng/mL of FGF2 in RPMI1640 culture medium.

Base medium 4 is a culture medium containing 2 volume % B27 (registered trademark) Supplement and 20 ng/mL of HGF in RPMI1640 culture medium.

Base medium 5 is a culture medium containing 20 ng/mL of oncostatin (oncostatin M) in Hepatocyte Culture Media (HCM) Bulletkit (registered trademark) minus EGF.

The compositions of base media 1 to 5 are given in Table 1.

TABLE 1

| base medium | culture medium | additives | content |
|---|---|---|---|
| 1 | RPMI1640 | B27 (registered trademark) Supplement, minus insulin | 2 vol % |
|  |  | BMP4 | 10 ng/mL |
|  |  | FGF2 | 20 ng/mL |
| 2 | RPMI1640 | B27 (registered trademark) Supplement, minus insulin | 2 vol % |

TABLE 1-continued

| base medium | culture medium | additives | content |
|---|---|---|---|
| 3 | RPMI1640 | B27 (registered trademark) Supplement | 2 vol % |
| | | BMP4 | 20 ng/mL |
| | | FGF2 | 10 ng/mL |
| 4 | RPMI1640 | B27 (registered trademark) Supplement | 2 vol % |
| | | HGF | 20 ng/mL |
| 5 | HCMBulletkit ® (Minus EGF) | oncostatin M | 20 ng/mL |

The following were used here: RPMI1640 from Life Technologies Corporation (Cat. No. GIBCO 11875-093), B27 (registered trademark) Supplement (minus insulin) from Life Technologies Corporation (Cat. No. A189956-01), BMP4 from Life Technologies Corporation (Cat. No. 0531120001), FGF2 from ReproCELL Inc. (Cat. No. RCHEOT002), and B27 (registered trademark) Supplement from Life Technologies Corporation (Cat. No. 17504-044). The HCMBulletkit (registered trademark) minus EGF is a culture medium provided by the addition of the additive factors—other than EGF—from an HCM SingleQuots kit (product from Lonza Ltd, Cat. No. CC-4182), which is an additive factor set, to hepatocyte Basal Medium (HBM, product from Lonza Ltd, Cat. No. CC-3199). Thus, it is a culture medium provided by the addition in prescribed proportions (precise concentrations not reported) of ascorbic acid, bovine serum albumin-fatty acid free (BSA-FAF), hydrocortisone, Transferrin, insulin, and GA-1000 (product containing gentamycin and amphotericin B) to the aforementioned HBM. The oncostatin M used was from R&D Systems, Inc. (Cat. No. 205-OM-010).

The iPS cells, which were the test cells, were seeded to 12-well plates coated with an extracellular matrix (Geltrex (registered trademark) in the present case). Using mTeSR1 (STEMCELL Technologies Inc.) for the culture medium, they were cultured (precultured) in a $CO_2$ incubator under conditions of 37° C. and 5% $CO_2$ until an appropriate cell density (here, a confluence of about at least 60% and not more than 70%) had been reached. Medium exchange was performed each day during this preculture.

The sample 1 obtained in Example 1 was then added to the culture medium and cultivation was carried out (main culture). Thus, the pluripotent stem cells were induced to myocardial cells (production of myocardial cells) by using the myocardial cell differentiation-inducing synthetic peptide obtained in Example 1 (sample 1) in place of the activin A in the method for inducing the differentiation of pluripotent stem cells into hepatocytes that is given in Non Patent Literature 3. The following were set up in the present example: a test section (referred to below as the activin A addition section) that used the same method as the method given in Non Patent Literature 3 for inducing the differentiation of pluripotent stem cells to hepatocytes using activin A; a test section (referred to below as the sample 1 addition section) that used the myocardial cell differentiation-inducing synthetic peptide of sample 1 in place of the activin A in the activin A addition section; and a control section to which neither the activin A nor the myocardial cell differentiation-inducing synthetic peptide was added. The specifics are given below. The culture conditions in this main culture are given schematically in FIG. 1.

First, the culture medium was exchanged to base medium 1 in the activin A addition section, the sample 1 addition section, and the control section. In the activin A addition section, activin A (R&D Systems, Inc., Cat. No. 338-AC-D50) was added to the culture vessel (i.e., to the base medium 1) in a quantity that provided an activin A concentration in the culture medium of 100 ng/mL. In the sample 1 addition section, the sample 1 peptide was added to the culture vessel (i.e., to the base medium 1) in an amount that provided a peptide concentration in the culture medium of 8 µM. Cultivation was carried out for 2 days in a $CO_2$ incubator under conditions of 37° C. and 5% $CO_2$.

After this cultivation for 2 days (i.e., the 2nd day after the start of the main culture), the culture medium was exchanged to base medium 2 in the activin A addition section, the sample 1 addition section, and the control section. In the activin A addition section, activin A was added to the culture vessel (i.e., to the base medium 2) in a quantity that provided an activin A concentration in the culture medium of 100 ng/mL. In the sample 1 addition section, the sample 1 peptide was added to the culture vessel (i.e., to the base medium 2) in an amount that provided a peptide concentration in the culture medium of 8 µM. Cultivation was carried out for 3 days in a $CO_2$ incubator under conditions of 37° C. and 5% $CO_2$.

After this cultivation for 3 days (i.e., the 5th day after the start of the main culture), the culture medium was exchanged to base medium 3 in the activin A addition section, the sample 1 addition section, and the control section. In the sample 1 addition section, the sample 1 peptide was added to the culture vessel (i.e., to the base medium 3) in an amount that provided a peptide concentration in the culture medium of 8 µM. Cultivation was carried out for 2 days in a $CO_2$ incubator under conditions of 37° C. and 5% $CO_2$.

After this cultivation for 2 days (i.e., the 7th day after the start of the main culture), the culture medium was exchanged to base medium 3 in the activin A addition section, the sample 1 addition section, and the control section, and cultivation was carried out for 3 days in a $CO_2$ incubator under conditions of 37° C. and 5% $CO_2$.

After this cultivation for 3 days (i.e., the 10th day after the start of the main culture), the culture medium was exchanged to base medium 4 in the activin A addition section, the sample 1 addition section, and the control section, and cultivation was carried out for 5 days in a $CO_2$ incubator under conditions of 37° C. and 5% $CO_2$.

After this cultivation for 5 days (i.e., the 15th day after the start of the main culture), the culture medium was exchanged to base medium 5 in the activin A addition section, the sample 1 addition section, and the control section, and cultivation was carried out for the indicated period of time in a $CO_2$ incubator under conditions of 37° C. and 5% $CO_2$.

The morphology of the cultured iPS cells in each test section was microscopically (optical microscope) observed (bright-field observation in the present case) each day after the start of the main culture. It was confirmed as a result of this microscopic observation that cells that beat periodically (beating cells) were present in the sample 1 addition section at the 9th day after the start of the main culture. The number of these beating cells present (abundance ratio) had increased in the sample 1 addition section at the 10th day after the start of the main culture in comparison to that for the sample 1 addition section at the 9th day after the start of the main culture. It was also confirmed that the number of beating cells present (abundance ratio) in the sample 1 addition section increased as the culture time during main culture increased. The presence of approximately 38 beating cells/well was confirmed for the sample 1 addition section at the 17th day after the start of the main culture. Videos were made (not shown here) of the beating cells present in the sample 1 addition section on the 24th day and 29th day after the start of the main culture.

On the other hand, the presence of these beating cells could not be confirmed for either the activin A addition section or the control section.

Tests were independently repeated a plurality of times using the same conditions as in the production of myocardial cells described above, and it was thereby confirmed at a probability of at least 95% that at least 1 beating cell was present (occurred) per 1 well in the 12-well plate in the sample 1 addition section. Typically, beginning with the confirmation of the presence of beating cells at around the 9th day after the start of the main culture, the number of beating cells present (abundance ratio) increased as the culture time during main culture increased. The number of beating cells (abundance ratio) confirmed to be present in the sample 1 addition section at the 17th day after the start of main culture was on average about 40 per 1 well of the 12-well plate.

On the other hand, the presence of beating cells was not confirmed when the tests were independently repeated a plurality of times using the same conditions as in the activin A addition section and the control section.

Example 3: Evaluation of the State of Expression of Myocardial Cell Marker Genes To check the state of expression of myocardial cell marker genes, cytoimmunostaining (fluorescent immunostaining) of proteins that are the gene products of myocardial marker genes was carried out on the cells in each of the test sections at the 16th day after the start of main culture. The expression of the following as myocardial marker genes was checked: myosin heavy chain (MHC), cardiac Troponin T (cTnT), tropomyosin (TM), and connexin 43 (Cx43).

First, the cells in each test section were subjected to a fixing treatment, a permeabilization treatment, and a blocking treatment. This fixing treatment, permeabilization treatment, and blocking treatment were carried out using a commercial kit (Image-iT Fixation/Permeabilization Kit, Life Technologies Corporation) in accordance with the manual provided with the kit.

Specifically, the culture medium was first removed from the culture vessel (12-well plate) for the cells in each test section on the 16th day after the start of the main culture (16th day after the addition of the myocardial cell differentiation-inducing synthetic peptide). The fixing treatment was performed by adding the fixative solution (Fixative Solution, contained 4 volume % formaldehyde in PBS (pH=7.3)) from the kit at 0.4 mL/well and holding at quiescence for 15 minutes at room temperature. This was followed by washing 3 times using the wash buffer (Wash Buffer, PBS, pH=7.4) from the kit at 0.5 mL/well.

A permeabilization treatment was then performed by adding the permeabilization solution (Permeabilization solution, contained 0.5 volume % Triton (registered trademark) X-100) from the kit at 0.5 mL/well and holding at quiescence for 15 minutes at room temperature. This was followed by washing three times with the wash buffer (0.5 mL/mL) from the kit.

After the cells in each well had been washed with PBS-T (PBS containing 0.25 volume % Triton (registered trademark) X-100), a blocking treatment was performed by adding the blocking solution (Blocking Solution, contained 3 weight/volume % (w/v %) BSA fraction V in DPBS (Dulbecco's PBS) (pH=7.4)) from the kit to each well and standing at quiescence overnight (about 18 hours) at 4° C.

After this blocking treatment, the primary antibody dilutions were added to each well followed by holding at quiescence for 2 hours at room temperature; the primary antibody dilutions were prepared by the dilution of the specified primary antibodies to a suitable antibody concentration using the blocking solution used in the blocking treatment.

The following primary antibodies were used as these primary antibodies: anti-myosin heavy chain antibody, anti-cardiac Troponin T antibody, anti-tropomyosin antibody, and anti-connexin 43 antibody. The details for the primary antibodies used in this example and the specific dilution ratios of these primary antibodies are given in Table 2. For the antibodies shown in Table 2, the anti-myosin heavy chain antibody was from R&D Systems, Inc., and the anti-cardiac Troponin T antibody, the anti-tropomyosin antibody, and the anti-connexin 43 antibody were from Abcam plc.

Here, these antibodies were diluted such that the anti-myosin heavy chain antibody and anti-cardiac Troponin T antibody were present at the prescribed dilution concentrations in a single primary antibody dilution, while the anti-tropomyosin antibody and anti-connexin 43 antibody were present at the prescribed dilution concentrations in another single primary antibody dilution. That is, a double staining was performed using the anti-myosin heavy chain antibody and the anti-cardiac Troponin T antibody, and a double staining was performed using the anti-tropomyosin antibody and the anti-connexin 43 antibody. In the following, the primary antibody dilution containing the anti-myosin heavy chain antibody and the anti-cardiac Troponin T antibody is also referred to as the primary antibody dilution A, while the primary antibody dilution containing the anti-tropomyosin antibody and the anti-connexin 43 antibody is also referred to as the primary antibody dilution B.

TABLE 2

| antibody | Product Name | Cat. No. | animal source | dilution ratio | antibody dilution |
| --- | --- | --- | --- | --- | --- |
| anti-myosin heavy chain antibody | Myosin Heavy Chain Antibody | MAB4470 | mouse | 100 | A |
| anti-cardiac Troponin T antibody | Anti-Cardiac Troponin T antibody | ab45932 | rabbit | 1000 | A |
| anti-tropomyosin antibody | Anti-Tropomyosin antibody [CH1] | ab7786 | mouse | 100 | B |
| anti-connexin 43 antibody | Anti-Connexin43/GJA1 antibody | ab11370 | rabbit | 1000 | B |

After the prescribed period of time had elapsed for the antigen-antibody reactions using these primary antibodies, the primary antibody dilutions were eliminated by washing with PBS. Using the blocking solution described above, a secondary antibody dilution was prepared in which the secondary antibody was diluted 1000×, and this secondary antibody dilution was added to each well and holding at quiescence in the dark was carried out for 1 hour at room temperature. Anti-mouse IgG antibody (goat origin, Life Technologies Corporation, 47759A) labeled with a fluorescent dye (Alexa Fluor (registered trademark) 488) and anti-rabbit IgG antibody (goat origin, Life Technologies Corporation, 1205993) labeled with a fluorescent dye (Alexa Fluor (registered trademark) 594) were used as the secondary antibodies, and these secondary antibodies were diluted such that the two secondary antibodies were present at the prescribed concentration in a single secondary antibody dilution.

After the prescribed period of time had elapsed, the secondary antibody dilution was removed by washing with PBS. After this cytoimmunostaining, the cells in each test section were mounted using a cover glass and Prolong (registered trademark) Gold Antifade Mountant with DAPI (Life Technologies Corporation, Cat. No. P-36931), which is a liquid mountant for preventing fading that contains DAPI.

After this cytoimmunostaining (fluorescent immunostaining) had been performed as described above, the cells in each test section were submitted to observation of the fluorescence using a confocal laser microscope.

The results of observation of the fluorescence using a confocal laser microscope are given in FIG. 2 and FIG. 3. These figures are fluorescence micrographs that examine the expression of myosin heavy chain, cardiac Troponin T, tropomyosin, and connexin 43 in each of the test sections. FIG. 2 shows the results of the examination of their state of expression using anti-myosin heavy chain antibody and anti-cardiac Troponin T antibody as the primary antibodies (i.e., primary antibody dilution A), while FIG. 3 shows the results of the examination of their state of expression using anti-tropomyosin antibody and anti-connexin 43 antibody as the primary antibodies (i.e., primary antibody dilution B). In both FIG. 2 and FIG. 3, the results for the sample 1 addition section are shown on the left and the results for the control section are shown on the right.

Specifically, the second from the top and the third from the top in FIG. 2 show the fluorescence images that result from an examination of the state of expression of myosin heavy chain (second from top) and cardiac Troponin T (third from the top) by the immunofluorescent antibody method described above. In addition, the second from the top and the third from the top in FIG. 3 show the fluorescence images that result from an examination of the state of expression of tropomyosin (second from the top) and connexin 43 (third from the top) by the immunofluorescent antibody method described above. The fourth photograph from the top in FIG. 2 and FIG. 3 is an image of nuclear staining by DAPI, and the topmost photograph in FIG. 2 and FIG. 3 is an image (photograph) that shows the results of optical microscopic observation (bright-field observation) of the same visual field as the fluorescent microscopic observations in the second, third, and fourth from the top. The lowermost image in FIG. 2 and FIG. 3 is an image provided by stacking (merging) the images in the second, third, and fourth from the top in each figure (the fluorescence images and the nuclear staining image).

As shown in FIG. 2 and FIG. 3, in the sample 1 addition section numerous cells were seen that exhibited substantially increased amounts of expression of myosin heavy chain, cardiac Troponin T, tropomyosin, and connexin 43 in comparison to the cells in the control section. The presence of cells that have differentiated into myocardial cells is thus shown for the sample 1 addition section, where the sample 1 peptide was added. This result agrees with the result in Example 2, where beating cells were observed in large numbers in the sample 1 addition section.

These results demonstrate that the herein disclosed method can induce the differentiation of pluripotent stem cells of human origin into myocardial cells, that is, that myocardial cells can be produced by supplying the herein disclosed myocardial cell differentiation-inducing synthetic peptide (i.e., a composition for producing myocardial cells that contains this peptide as an effective ingredient) to pluripotent stem cells (typically by supply to the culture medium containing these cells). It was also confirmed that this supply of the myocardial cell differentiation-inducing synthetic peptide to the target pluripotent stem cells can be executed by using the synthetic peptide in place of activin A in the method for inducing the differentiation of human pluripotent stem cells to hepatocytes using the activin A.

These results also demonstrate that the herein disclosed myocardial cell differentiation-inducing synthetic peptide (i.e., a composition for producing myocardial cells that contains this peptide as an effective ingredient) is a peptide (composition) that can induce the differentiation of pluripotent stem cells into myocardial cells.

INDUSTRIAL APPLICABILITY

As has been described in the preceding, the herein disclosed method for producing myocardial cells can efficiently produce myocardial cells from pluripotent stem cells. In addition, the herein disclosed myocardial cell differentiation-inducing synthetic peptide has a myocardial cell differentiation-inducing capacity that causes the differentiation of pluripotent stem cells into myocardial cells and as a consequence can be advantageously used for the purpose of producing myocardial cells by inducing the differentiation of targeted pluripotent stem cells (particularly iPS cells of human origin). Accordingly, the herein disclosed composition for producing myocardial cells can be advantageously utilized, for example, as a composition for application in regenerative medical therapies.

(Sequence Listing Free Text)
    SEQ ID NOs:1 to 26 synthetic peptide

The invention claimed is:

1. A method for producing myocardial cells from human pluripotent stem cells in vitro, the method comprising:
   preparing a cell culture of human pluripotent stem cells;
   (A) culturing the human pluripotent stem cells for about 2 days on a first culture medium consisting of a synthetic peptide, Bone Morphogenetic Protein 4 (BMP4) and Fibroblast Growth Factor 2 (FGF2) in a culture medium, wherein the synthetic peptide comprises: a myocardial cell differentiation-inducing peptide sequence consisting of the amino acid sequence of SEQ ID NO: 16 or the amino acid sequence of SEQ ID NO: 17, and a membrane permeable peptide sequence consisting of the amino acid sequence of SEQ ID NO: 7; and the total number of amino acid residues constituting the synthetic peptide is not more than 50;
   (B) culturing the cells provided by (A), for about 3 days, on a second culture medium containing the synthetic peptide in a culture medium;
   (C) culturing the cells provided by (B), for about 2 days, on a third culture medium containing the synthetic peptide, BMP4, and FGF2 to provide differentiated myocardial cells exhibiting increased levels of expression of at least one or two myocardial cell marker genes selected from the group consisting of myosin heavy chain (MHC), cardiac Troponin T (cTnT), tropomyosin (TM), and connexin 43 (Cx43) as compared to control cells;
   (D) separating the differentiated myocardial cells exhibiting said myocardial cell marker from the cells provided after the culture of step (C); and
   E) harvesting the separated myocardial cells.

2. The method for producing myocardial cells according to claim 1, between the culture step (C) and the separating, further comprising,
   culturing the cells provided by (C), for at least 2 days, on a fourth culture medium containing BMP4, and FGF2 in a culture medium.

3. The method for producing myocardial cells according to claim 1, wherein between the culture step (C) and the step (D), further comprising the following culture steps consisting of (F), (G), and (H):
   (F) culturing the cells provided by (C), for about 3 days, on a fourth culture medium containing BMP4, and FGF2 in a culture medium;
   (G) culturing the cells provided by (F), for about 5 days, on a fifth culture medium containing Hepatocyte Growth Factor (HGF) in a culture medium; and,
   (H) culturing the cells provided by (G), for an indicated period of time, on a sixth culture medium containing oncostatin M in a culture medium.

4. The method for producing myocardial cells according to claim 1, wherein the total number of amino acid residues constituting the synthetic peptide is not more than 30.

5. The method for producing myocardial cells according to claim 1, wherein the synthetic peptide has the membrane-permeable peptide sequence at the N-terminal side or C-terminal side of the amino acid sequence of the myocardial cell differentiation-inducing peptide sequence.

6. The method for producing myocardial cells according to claim 1, wherein the synthetic peptide has 1, 2, or 3 glycine residues as a linker between the myocardial cell differentiation-inducing peptide sequence and the membrane-permeable peptide sequence.

7. The method for producing myocardial cells according to claim 1, wherein the synthetic peptide has the amino acid sequence as set forth in SEQ ID NO: 26.

8. The method for producing myocardial cells according to claim 1, wherein the FGF2 of the culture step (A) is in a RPMI1640 culture medium.

9. The method for producing myocardial cells according to claim 1, wherein the synthetic peptide of the culture step (B) is in a RPMI1640 culture medium.

10. The method for producing myocardial cells according to claim 1, wherein the FGF2 of the culture step (C) is in a RPMI1640 culture medium.

11. The method for producing myocardial cells according to claim 2, wherein the FGF2 of the fourth culture medium is in a RPMI1640 culture medium.

12. The method for producing myocardial cells according to claim 3, wherein the FGF2 of culture step (F) is in a RPMI1640 culture medium.

13. The method tor producing myocardial cells according to claim 3, wherein the HGF of culture step (G) is in a RPMI 1640 culture medium.

14. The method for producing myocardial cells according to claim 3, wherein the oncostatin M is in a culture medium for hepatocyte, without EGF.

* * * * *